(12) United States Patent
Kim et al.

(10) Patent No.: US 11,263,498 B2
(45) Date of Patent: Mar. 1, 2022

(54) METHOD AND SYSTEM FOR PROVIDING INFORMATION RELATED TO A STATUS OF AN OBJECT IN A REFRIGERATOR

(71) Applicant: SAMSUNG ELECTRONICS CO., LTD., Suwon-si (KR)

(72) Inventors: Jaehwan Kim, Suwon-si (KR); Oleksandr Baiev, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 16/572,075

(22) Filed: Sep. 16, 2019

(65) Prior Publication Data

US 2020/0097776 A1    Mar. 26, 2020

(30) Foreign Application Priority Data

Sep. 21, 2018    (KR) .................. 10-2018-0114377

(51) Int. Cl.
*G06T 7/10*    (2017.01)
*G06K 9/62*    (2022.01)
(Continued)

(52) U.S. Cl.
CPC ......... *G06K 9/6288* (2013.01); *G01N 33/025* (2013.01); *G06T 7/0002* (2013.01);
(Continued)

(58) Field of Classification Search
CPC .. F25D 2700/06; F25D 2500/06; F25D 29/00; G06K 9/6288; G06K 2209/17;
(Continued)

(56) References Cited

U.S. PATENT DOCUMENTS 5,691,684 A * 11/1997 Murrah ............... G06Q 10/087
                                                    235/385
6,050,412 A *  4/2000 Clough ............... B65D 65/403
                                                    206/423
(Continued)

FOREIGN PATENT DOCUMENTS

JP    2016-133296 A    7/2016
JP    2016148503 A     8/2016
(Continued)

OTHER PUBLICATIONS

International Search Report and Written Opinion (PCT/ISA/210 and PCT/ISA/237), dated Dec. 26, 2019 by International Searching Authority in International Application No. PCT/KR2019/011618.
(Continued)

*Primary Examiner* — Philip P. Dang
(74) *Attorney, Agent, or Firm* — Sughrue Mion, PLLC

(57) ABSTRACT

A method of providing information related to a state of an object in a refrigerator includes obtaining a first camera image including at least one object kept in the refrigerator through a camera arranged in the refrigerator, obtaining environmental information in the refrigerator through an environmental sensor arranged in the refrigerator, predicting information related to a current state of the at least one object by applying the first camera image including the at least one object and the environmental information in the refrigerator to an artificial intelligence (AI) model; and providing the information related to the current state of the at least one object.

22 Claims, 30 Drawing Sheets

(51) Int. Cl.
　　　*G06T 7/00*　　　(2017.01)
　　　*G06T 7/70*　　　(2017.01)
　　　*G01N 33/02*　　(2006.01)
　　　*H04N 5/232*　　(2006.01)
　　　*H04L 67/12*　　(2022.01)

(52) U.S. Cl.
　　　CPC .............. *G06T 7/70* (2017.01); *G06T 7/97* (2017.01); *H04N 5/23299* (2018.08); *G06K 2209/17* (2013.01); *H04L 67/12* (2013.01)

(58) Field of Classification Search
　　　CPC ........... G06T 7/0002; G06T 7/70; G06T 7/97; G01N 33/025; H04N 5/23299; H04L 67/12
　　　See application file for complete search history.

(56) References Cited

U.S. PATENT DOCUMENTS

| | | | | |
|---|---|---|---|---|
| 6,204,763 | B1* | 3/2001 | Sone | A47G 29/141 221/2 |
| 7,218,315 | B2* | 5/2007 | Takeuchi | G06F 1/1654 345/204 |
| 7,447,330 | B2* | 11/2008 | Yamasaki | H04N 5/2251 382/100 |
| 7,755,566 | B2* | 7/2010 | Hoisko | H04N 1/32128 345/1.2 |
| 7,920,898 | B2* | 4/2011 | Callaghan | G06K 7/10881 455/557 |
| 8,004,571 | B2* | 8/2011 | Yamashita | H04N 7/181 348/211.12 |
| 8,156,748 | B2* | 4/2012 | Ashrafzadeh | F25C 5/187 62/137 |
| 8,164,567 | B1* | 4/2012 | Barney | A63F 13/219 345/158 |
| 8,248,237 | B2* | 8/2012 | Fitzgerald | H04W 12/126 340/571 |
| 8,381,409 | B2* | 2/2013 | Knoke | G01B 11/27 33/288 |
| 8,713,949 | B2* | 5/2014 | Chase | F25C 5/187 62/137 |
| 9,013,273 | B2* | 4/2015 | Oh | F25D 29/00 340/6.1 |
| 9,032,745 | B2* | 5/2015 | Ashrafzadeh | F25C 5/187 62/135 |
| 9,147,298 | B2* | 9/2015 | Ricci | G06K 9/00268 |
| 9,719,720 | B2* | 8/2017 | Seo | F25D 29/00 |
| 9,821,344 | B2* | 11/2017 | Zsigmond | G06Q 30/0601 |
| 9,959,628 | B2* | 5/2018 | Mutti | G06K 9/2018 |
| 10,034,066 | B2* | 7/2018 | Tran | G06K 9/00355 |
| 10,255,689 | B2* | 4/2019 | Lee | H04N 5/232122 |
| 10,355,730 | B1* | 7/2019 | Zalewski | H04W 76/14 |
| 10,410,177 | B2* | 9/2019 | Causey | G06Q 30/0207 |
| 10,525,349 | B2* | 1/2020 | Nishimaki | G06T 7/70 |
| 10,655,907 | B2* | 5/2020 | Hwang | G05D 23/1934 |
| 2005/0134710 | A1* | 6/2005 | Nomura | H04N 5/23245 348/240.99 |
| 2006/0274153 | A1* | 12/2006 | Levien | H04N 1/00132 348/207.1 |
| 2007/0139529 | A1* | 6/2007 | Levien | G06T 1/00 348/220.1 |
| 2008/0014917 | A1* | 1/2008 | Rhoads | G06Q 30/06 455/422.1 |
| 2008/0309617 | A1* | 12/2008 | Kong | G06F 3/0482 345/157 |
| 2009/0021573 | A1* | 1/2009 | Kim | H04N 21/4126 348/14.02 |
| 2009/0315671 | A1* | 12/2009 | Gocho | H04N 1/4426 340/5.8 |
| 2010/0231506 | A1* | 9/2010 | Pryor | F24C 15/2021 345/156 |
| 2010/0283573 | A1* | 11/2010 | Yum | G06Q 10/087 340/3.1 |
| 2012/0061155 | A1* | 3/2012 | Berger | B25J 5/007 180/21 |
| 2012/0208466 | A1* | 8/2012 | Park | G06F 1/1601 455/41.3 |
| 2012/0218301 | A1* | 8/2012 | Miller | G02B 27/0172 345/633 |
| 2012/0251079 | A1* | 10/2012 | Meschter | G16H 40/67 386/278 |
| 2013/0015753 | A1* | 1/2013 | Son | B01D 46/00 312/405 |
| 2013/0063550 | A1* | 3/2013 | Ritchey | G06F 3/015 348/36 |
| 2013/0076936 | A1* | 3/2013 | Yoshida | H04N 5/23293 348/222.1 |
| 2014/0095479 | A1* | 4/2014 | Chang | G06F 16/335 707/722 |
| 2014/0310031 | A1* | 10/2014 | Ricci | G06Q 30/0265 705/5 |
| 2014/0310788 | A1* | 10/2014 | Ricci | G06F 21/31 726/6 |
| 2015/0018979 | A1* | 1/2015 | Tomii | H04L 12/2803 700/19 |
| 2016/0057394 | A1* | 2/2016 | Marutani | H04N 1/00095 348/143 |
| 2016/0138857 | A1 | 5/2016 | Klingshirn | |
| 2016/0182864 | A1* | 6/2016 | Izawa | H04N 5/232939 348/159 |
| 2017/0337425 | A1* | 11/2017 | Lee | G06K 9/00744 |
| 2018/0053140 | A1 | 2/2018 | Baca et al. | |
| 2018/0143756 | A1* | 5/2018 | Mildrew | G06T 19/003 |
| 2018/0165854 | A1* | 6/2018 | Du | G06N 20/00 |
| 2018/0210418 | A1 | 7/2018 | Choi et al. | |
| 2018/0239319 | A1 | 8/2018 | Abdoo et al. | |
| 2019/0011965 | A1* | 1/2019 | Seyed | G06F 1/206 |

FOREIGN PATENT DOCUMENTS

| | | |
|---|---|---|
| KR | 10-2018-0045230 A | 5/2018 |
| KR | 10-2018-0047714 A | 5/2018 |
| KR | 10-1864252 B1 | 6/2018 |
| KR | 10-2018-0088116 A | 8/2018 |

OTHER PUBLICATIONS

Communication dated Jul. 22, 2021, issued by the European Patent Office in European Application No. 19862517.0.

Communication dated Nov. 25, 2021 by the European Patent Office in European Patent Application No. 19862517.0.

* cited by examiner

FIG. 5
LEARNING DATA (310)
| | CAMERA IMAGE (501) | SPECTROMETRIC IMAGE (502) | ENVIRONMENTAL INFORMATION (503) | | | CONSUMABLE PERIOD (504) |
|---|---|---|---|---|---|---|
| | | | GAS DETECTION QUANTITY | TEMPERATURE | HUMIDITY | |
| 1 |  |  | 50μm | 4°C | 40% | 2-9 DAYS |
| 2 |  |  | 125μm | 3°C | 35% | 0-4 DAYS |
| 3 |  |  | 70μm | 4°C | 21% | 0-16 DAYS |
| 4 |  | 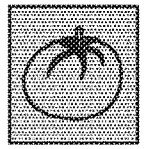 | 0μm | 2°C | 42% | 8-25 DAYS |
| ⋮ | ⋮ | ⋮ | ⋮ | ⋮ | ⋮ | ⋮ |

FIG. 19
FIRST TYPE OF METHOD(1910):
DETECT CAMERA IMAGE WHEN DOOR OF REFRIGERATOR IS OPENED AND CLOSED
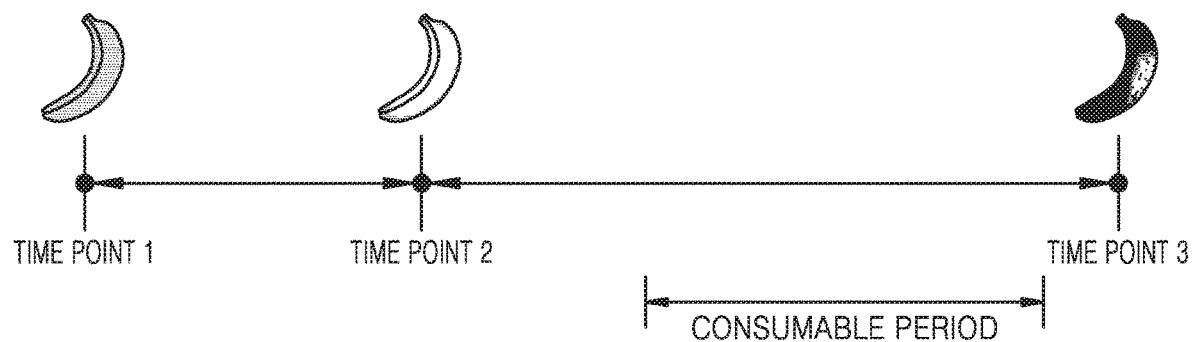
SECOND TYPE OF METHOD (1920):
ADJUST IMAGE DETECTION INTERVAL BASED ON STATE OF OBJECT
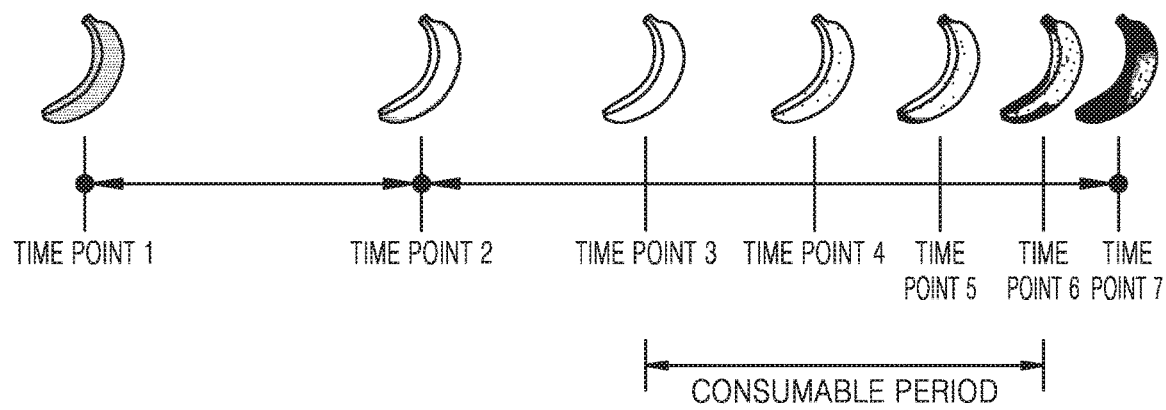

METHOD AND SYSTEM FOR PROVIDING INFORMATION RELATED TO A STATUS OF AN OBJECT IN A REFRIGERATOR

CROSS-REFERENCE TO RELATED APPLICATION

This application is based on and claims priority under 35 U.S.C. § 119 to Korean Patent Application No. 10-2018-0114377, filed on Sep. 21, 2018, in the Korean Intellectual property Office, the disclosure of which is incorporated by reference herein in its entirety.

BACKGROUND

1. Field

The disclosure relates to an artificial intelligence (AI) system using a machine learning algorithm, such as deep learning, etc., and an application of the AI system, and more particularly, to a method and a system for providing information related to a state of an object stored in a refrigerator by using the AI system.

2. Description of Related Art

An artificial intelligence (AI) system is a computer system with human level intelligence, and unlike a previous rule-based smart system, the AI system is a system that trains itself, decides, and becomes increasingly smarter. The more the AI system is used, the higher the recognition rate of the AI system and the AI system may more accurately understand a user's taste. Thus, the previous rule-based smart system has been gradually replaced by a deep learning-based AI system.

AI technologies are composed of machine learning (for example, deep learning) and element technologies using the machine learning.

Machine learning is an algorithm technology that classifies/learns characteristics of input data on its own. The element technology is a technology that simulates functions of the human brain, such as recognition, determination, etc., by using machine learning algorithms, such as deep learning, etc., and includes technical fields of linguistic understanding, visual comprehension, inference/prediction, knowledge representation, operation control, etc.

AI technology is applied to various fields as follows. The linguistic understanding is a technology to recognize and apply/process human language/characters and includes processing of natural language, machine translation, a conversation system, query response, speech recognition/synthesis, etc. The visual comprehension is a technology to recognize and process objects as in human vision and includes object recognition, object detection, image search, human recognition, scene understanding, spatial understanding, image enhancement, etc. The inference prediction is a technology to examine and logically infer and predict information and includes inference based on knowledge/probabilities, optimization prediction, preference-based planning, recommendation, etc. The knowledge representation is a technology to automatically process human experience data into knowledge data and includes knowledge establishment (data generation/classification), knowledge management (data usage), etc. The operation control is a technology to control autonomous driving of a vehicle and motions of a robot and includes motion control (navigation, collision avoidance, driving), manipulation control (behavior control), etc.

SUMMARY

Provided are a method and a system for providing information (for example, consumable period information, the freshness, the ripeness, etc.) related to a current state of at least one object kept in a refrigerator, by applying a camera image in the refrigerator and information (for example, temperature information, humidity information, or odor information) of an environment in the refrigerator to an artificial intelligence (AI) model.

Provided are a method and a system for providing information related to a current state of at least one object kept in a refrigerator by using a spectrometric sensor as well as a camera and an environmental sensor.

Additional aspects will be set forth in part in the description which follows and, in part, will be apparent from the description, or may be learned by practice of the presented embodiments of the disclosure.

According to an embodiment of the disclosure, a method of providing information related to a state of an object in a refrigerator includes obtaining a first camera image including at least one object kept in the refrigerator through a camera arranged in the refrigerator, obtaining environmental information in the refrigerator through an environmental sensor arranged in the refrigerator, predicting information related to a current state of the at least one object by applying the first camera image including the at least one object and the environmental information in the refrigerator to an artificial intelligence (AI) model, and providing the information related to the current state of the at least one object.

The providing of the information related to the current state of the at least one object may include providing information about a consumable period of the at least one object.

The providing of the information related to the current state of the at least one object may include providing information about a ripeness or a freshness of the at least one object.

The environmental sensor may include at least one of a temperature sensor, a humidity sensor, or an odor sensor, and the obtaining of the environmental information in the refrigerator may include obtaining at least one of temperature information, humidity information, or odor information in the refrigerator.

The obtaining of the environmental information in the refrigerator may include obtaining temperature information of a temperature around the at least one object by using a temperature sensor, and the predicting of the information related to the current state of the at least one object may include predicting the information related to the current state of the at least one object by applying the first camera image and the temperature information to the AI model.

The obtaining of the environmental information in the refrigerator may include obtaining odor information of the at least one object by using an odor sensor arranged to be adjacent to the at least one object, and the predicting of the information related to the current state of the at least one object may include predicting the information related to the current state of the at least one object by applying the first camera image and the odor information to the AI model.

The predicting of the information related to the current state of the at least one object may include obtaining a spectrometric image with respect to the at least one object by using a spectrometric sensor arranged in the refrigerator; and predicting the information related to the current state of the at least one object by applying the first camera image, the spectrometric image, and the environmental information in the refrigerator to the AI model.

The predicting of the information related to the current state of the at least one object may include determining whether a gas detection quantity measured by at least one odor sensor from among a plurality of odor sensors arranged in the refrigerator exceeds a critical value, when the gas detection quantity exceeds the critical value, generating an odor distribution map based on odor information obtained from the plurality of odor sensors, and comparing the first camera image comprising the at least one object with the odor distribution map and identifying a first object of the at least one object including a spoilage probability that is greater than a reference value.

The identifying of the first object may include obtaining spectrometric information about the first object by using a spectrometric sensor arranged in the refrigerator; and determining a degree of spoilage of the first object by using the spectrometric information.

The method may further include when the first object is totally or partially hidden by a second object of the at least one object in the first camera image, providing notification information about a location where the first object is kept in the refrigerator.

The method may further include controlling a position of the camera to capture the identified first object.

The obtaining of the first camera image may include obtaining the first camera image comprising the at least one object at a first time point through the camera, and the method may further include obtaining a second camera image comprising the at least one object at a second time point, which is after the first time point, through the camera, obtaining information related to a state of the at least one object at the second time point and a degree of a state change of the at least one object between the first time point and the second time point, by applying the first camera image, the second camera image, and environmental information at the second time point to the AI model, and controlling an image detection interval of the camera, based on at least one of the information related to the state of the at least one object at the second time point or the degree of the state change of the at least one object.

According to another embodiment of the disclosure, a refrigerator includes a camera configured to obtain a first camera image including at least one object kept in the refrigerator, an environmental sensor configured to obtain environmental information in the refrigerator, and a processor configured to predict information related to a current state of the at least one object by applying the first camera image and the environmental information in the refrigerator to an artificial intelligence (AI) model, and an outputter configured to provide the information related to the current state of the at least one object.

The information related to the current state of the at least one object may include at least one of information about a consumable period of the at least one object, information about a ripeness of the at least one object, or information about a freshness of the at least one object.

The environmental sensor may include a temperature sensor, and the processor may be further configured to obtain temperature information of a temperature around the at least one object by using the temperature sensor, and predict the information related to the current state of the at least one object by applying the first camera image and the temperature information to the AI model.

The environmental sensor may include an odor sensor arranged to be adjacent to the at least one object, and the processor may be further configured to obtain odor information of the at least one object by using the odor sensor, and predict the information related to the current state of the at least one object by applying the first camera image comprising the at least one object and the odor information of the at least one object to the AI model.

The processor may be further configured to obtain a spectrometric image about the at least one object by using a spectrometric sensor arranged in the refrigerator, and predict the information related to the current state of the at least one object by applying the first camera image, the spectrometric image, and the environmental information in the refrigerator to the AI model.

The processor may be further configured to determine whether a gas detection quantity measured by at least one odor sensor from among a plurality of odor sensors arranged in the refrigerator exceeds a critical value, generate an odor distribution map based on odor information obtained from the plurality of odor sensors, when the gas detection quantity exceeds the critical value, and compare the first camera image comprising the at least one object with the odor distribution map and identify a first object of the at least one object including a spoilage probability that is greater than a reference value.

The processor may be further configured to obtain spectrometric information about the first object by using a spectrometric sensor arranged in the refrigerator, and determine a degree of spoilage of the first object by using the spectrometric information.

According to another embodiment of the disclosure, a computer program product includes a recording medium having recorded thereon a program to execute an operation of obtaining a first camera image including at least one object kept in a refrigerator through a camera arranged in the refrigerator, an operation of obtaining environmental information in the refrigerator through an environmental sensor arranged in the refrigerator, an operation of predicting information related to a current state of the at least one object by applying the first camera image including the at least one object and the environmental information in the refrigerator to an artificial intelligence (AI) model, and an operation of providing the information related to the current state of the at least one object.

BRIEF DESCRIPTION OF THE DRAWINGS

The above and other aspects, features, and advantages of certain embodiments of the disclosure will be more apparent from the following description taken in conjunction with the accompanying drawings, in which:

FIG. 5 is a view for describing learning data according to an embodiment of the disclosure;

FIG. 19 is a view for describing an interval of image detection of a camera, according to an embodiment of the disclosure;

DETAILED DESCRIPTION

Figure 1:
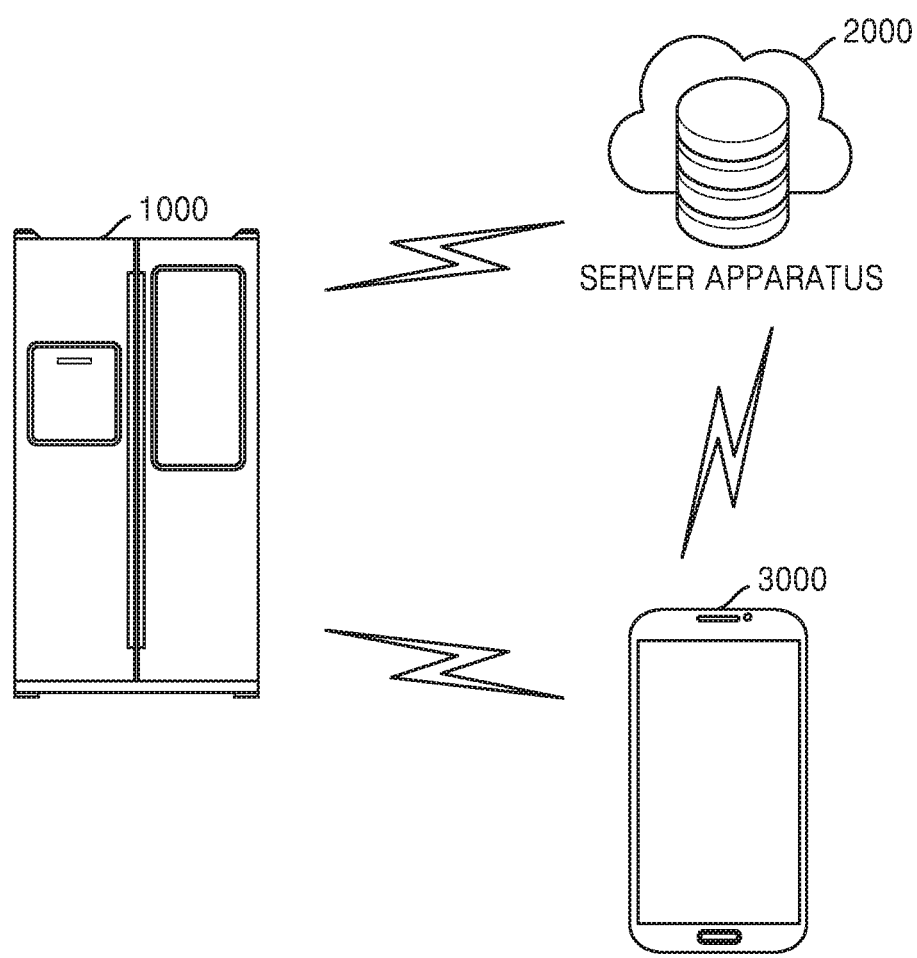
FIG. 1 is a view for describing a system for providing information related to a state of an object in a refrigerator, according to an embodiment of the disclosure.

The terms used in this specification will be briefly described and embodiments of the disclosure will be described in detail.

The terms used in the disclosure are selected from among common terms that are currently widely used in consideration of their function in the disclosure. However, the terms may be different according to an intention of one of ordinary skill in the art, a precedent, or the advent of new technology. Also, in particular cases, the terms are discretionally selected by the applicant of the disclosure, and the meaning of those terms will be described in detail in the corresponding part of the detailed description. Therefore, the terms used in the disclosure are not merely designations of the terms, but the terms are defined based on the meaning of the terms and content throughout the disclosure.

Throughout the specification, when a part "includes" an element, it is to be understood that the part additionally includes other elements rather than excluding other elements as long as there is no particular opposing recitation. Also, the terms described in the specification, such as "unit," "module," etc., denote a unit processing at least one function or operation, which may be implemented as hardware or software or a combination thereof.

Hereinafter, embodiments of the disclosure will now be described more fully with reference to the accompanying drawings for one of ordinary skill in the art to be able to perform the disclosure without any difficulty. The disclosure may, however, be embodied in many different forms and should not be construed as being limited to the embodiments of the disclosure set forth herein. Also, parts in the drawings unrelated to the detailed description are omitted to ensure clarity of the disclosure. Like reference numerals in the drawings denote like elements. Throughout the disclosure, the expression "at least one of a, b or c" indicates only a, only b, only c, both a and b, both a and c, both b and c, all of a, b, and c, or variations thereof.

FIG. 1 is a view for describing a system for providing information related to a state of an object in a refrigerator, according to an embodiment of the disclosure.

Referring to FIG. 1, the system (hereinafter, the information provision system) for providing the information related to the state of the object in the refrigerator, according to an embodiment of the disclosure, may include a refrigerator 1000, a server apparatus 2000, and a mobile terminal 3000. However, not all illustrated components are essential components. The information provision system may be realized by including more components than the illustrated components or by including less components than the illustrated components. For example, the information provision system may be realized by including the refrigerator 1000 and the server apparatus 2000, by including the refrigerator 1000 and the mobile terminal 3000, or by including only the refrigerator 1000. Each of the components will be described.

The refrigerator 1000 according to an embodiment of the disclosure may be an electronic device (or a home appliance device) refrigerating or freezing food. The refrigerator 1000 may store not only the food, but also medicines, alcoholic liquors, cosmetics, etc.

The refrigerator 1000 according to an embodiment of the disclosure may provide information related to a state of an object kept in the refrigerator 1000. In this specification, the object is an element which may be kept in the refrigerator 1000 and may include, for example, food (for example, fresh food items, such as fruits, vegetables, etc., cooked food items, processed products, condiments, and retort foods), medicines, alcoholic liquors, cosmetics, etc., but it is not limited thereto.

According to an embodiment of the disclosure, the refrigerator 1000 may be equipped with at least one camera for identifying an inner space of the refrigerator 1000. The refrigerator 1000 may obtain an image of an object kept in each shelf by using the at least one camera. The refrigerator 1000 may predict a current state of the object by using the image obtained through the at least one camera and environmental information in the refrigerator 1000 and provide information related to the current state of the object to a user. For example, the refrigerator 1000 may provide information (for example, an expected disposal date, etc.) about a consumable period of the object, the freshness or the ripeness of the object, etc., to the user.

Thus, according to an embodiment of the disclosure, the refrigerator 1000 may provide the information (for example, an expected disposal date, etc.) about the consumable period of the object to the user before the corresponding object gets spoiled, thereby driving the user to consume the object before the object is disposed, and improving the usability of the objects stored in the refrigerator 1000. A method performed by the refrigerator 1000 to provide the information related to the state of the object, according to an embodiment of the disclosure, will be described in detail below with reference to FIG. 2.

According to an embodiment of the disclosure, the refrigerator 1000 may include a display. In this case, the refrigerator 1000 may provide the information related to the state of the object kept in the refrigerator 1000 to the user via the display. According to another embodiment of the disclosure, the refrigerator 1000 may provide the information related to the state of the object to the user via the mobile terminal 3000 with respect to which a communication link is established. An operation, performed by the refrigerator 1000, of providing the information related to the state of the object via the mobile terminal 3000 will be described in detail below with reference to FIG. 11.

According to an embodiment of the disclosure, the refrigerator 1000 may include an artificial intelligence (AI) model for predicting a state of an object. According to an embodiment of the disclosure, the refrigerator 1000 may directly generate or refine the AI model by using learning data. Also, the refrigerator 1000 may receive an AI model trained by the server apparatus 2000 from the server apparatus 2000 and store the AI model.

According to an embodiment of the disclosure, the refrigerator 1000 may include a communication interface for performing communication with an external device. According to an embodiment of the disclosure, the refrigerator 1000 may perform communication with the server apparatus 2000 or the mobile terminal 3000 through the communication interface. The communication interface may include a short-range wireless communication interface, a mobile communication interface, etc. The short-range wireless communication interface may include, but is not limited to, a Bluetooth communication interface, a Bluetooth low energy (BLE) communication interface, a near field communication interface, a WLAN (Wi-Fi) communication interface, a Zigbee communication interface, an infrared data association (IrDA) communication interface, a Wi-Fi direct (WFD) communication interface, a ultra wideband (UWB) communication interface, an ANT+ communication interface.

According to an embodiment of the disclosure, the server apparatus 2000 may include an AI processor. The AI processor may train an artificial neural network to generate the AI model for predicting a state of an object. To "train" the artificial neural network may denote to generate an arithmetic model capable of performing optimal decision making via connection of neurons included in the artificial neural network, while appropriately changing the weight based on data. The operation performed by the server apparatus 2000 or the refrigerator 1000 to train the artificial neural network and generate the AI model will be described in detail below with reference to FIG. 3.

According to an embodiment of the disclosure, the server apparatus 2000 may include a communication interface for performing communication with an external device. According to an embodiment of the disclosure, the server apparatus 2000 may perform communication with the refrigerator 1000 or the mobile terminal 3000 via the communication interface. According to an embodiment of the disclosure, the refrigerator 1000 may transmit identification information of the refrigerator 1000 or identification information (login information) of a user to the server apparatus 2000 and may access the server apparatus 2000 by receiving authentication with respect to the identification information of the refrigerator 1000 or the identification information (login information) of the user from the server apparatus 2000.

The mobile terminal 3000 may be a device connected with the refrigerator 1000 with the same account information. The mobile terminal 3000 may be directly connected with the refrigerator 1000 via a short-range communication link or may be indirectly connected with the refrigerator 1000 via the server apparatus 2000.

The mobile terminal 3000 according to an embodiment of the disclosure may be realized in various forms. For example, the mobile terminal 3000 described in this specification may include, but is not limited to, a digital camera, a smartphone, a laptop computer, a tablet personal computer (PC), an electronic book terminal, a digital broadcasting terminal, a personal digital assistant (PDA), a portable multimedia player (PMP), a navigation apparatus, an MP3 player. For example, the mobile terminal 3000 may be a device wearable to a user. The wearable device may include at least one of an accessory-type device (for example, a watch, a ring, a bracelet, an anklet, a necklace, glasses, contact lenses, etc.) a head-mounted-device (HMD), a fabric or clothing-integral device (e.g., electronic clothing), a body-mounted-device (e.g., a skin pad), or a biometric transplant device (e.g., an implantable circuit). Hereinafter, for convenience of explanation, an example in which the mobile terminal 3000 is a smartphone will be described.

Figure 2:
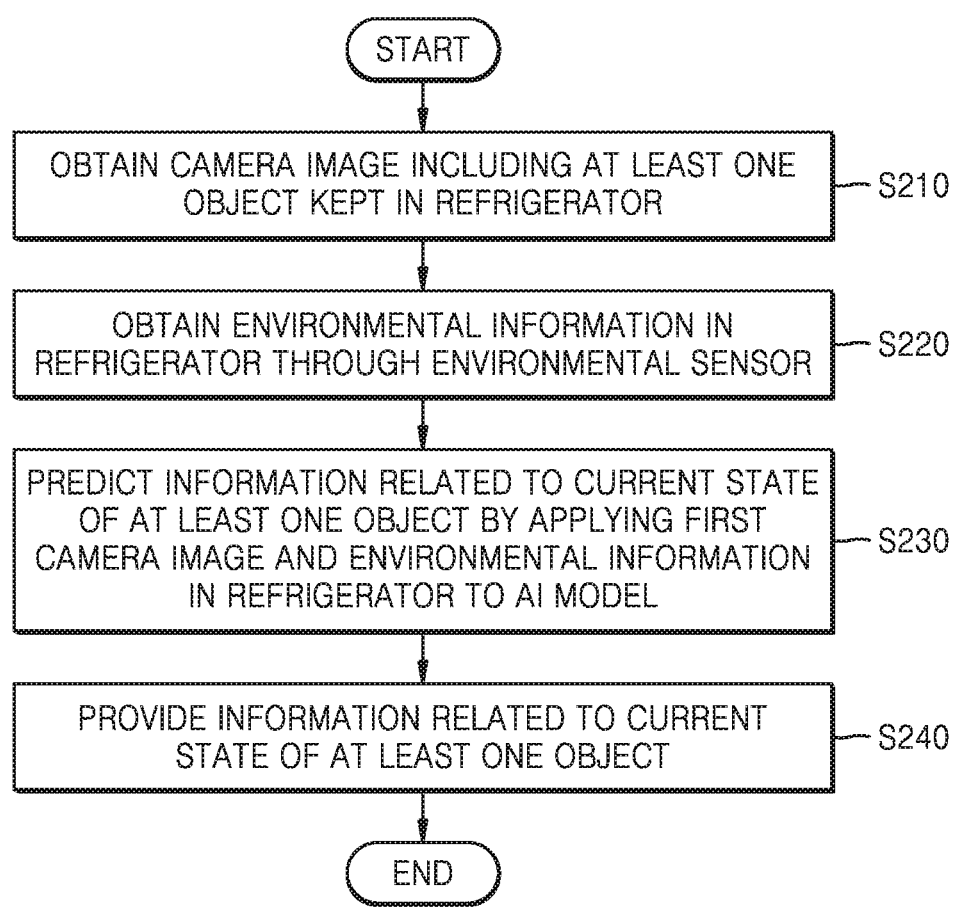
FIG. 2 is a flowchart of a method of providing information related to a state of an object in a refrigerator, according to an embodiment of the disclosure.

FIG. 2 is a flowchart of a method of providing information related to a state of an object in a refrigerator, according to an embodiment of the disclosure.

In operation S210, the refrigerator 1000 may obtain a camera image including at least one object kept in the refrigerator 1000 via a camera arranged in the refrigerator 1000.

According to an embodiment of the disclosure, the camera image may be an RGB image. Also, according to an embodiment of the disclosure, the camera image may include one object or a plurality of objects.

According to an embodiment of the disclosure, a plurality of cameras may be arranged in the refrigerator 1000. For example, depending on the size of the refrigerator 1000, a camera may be installed on each of shelves. When the plurality of cameras are arranged, the refrigerator 1000 may obtain a plurality of camera images. For example, the refrigerator 1000 may obtain a first camera image including first objects kept in a first shelf by using a first camera, obtain a second camera image including second objects kept in a second shelf by using a second camera, and a third camera image including third objects kept in a third shelf by using a third camera.

Meanwhile, the camera image may be an image generated by connecting the plurality of camera images. For example, the camera image may be a panorama image in which the first camera image, the second camera image, and the third camera image are connected.

According to an embodiment of the disclosure, the refrigerator 1000 may obtain the camera image by using the camera after a predetermined time period (for example, after three (3) seconds after a door of the refrigerator 1000 is closed) after a user opens or closes the door. In this case, because the objects kept in the refrigerator 1000 may be changed due to the user's opening and closing of the door of the refrigerator, a real time image of the changed objects may be obtained.

According to an embodiment of the disclosure, the refrigerator 1000 may obtain the camera image by using the camera at a predetermined time interval. For example, the refrigerator 1000 may obtain the camera image by using the camera at a time interval of three (3) hours.

According to an embodiment of the disclosure, the refrigerator 1000 may adjust an interval at which the camera detects the image, according to a state of the object. For example, when the object starts to get spoiled, the refrigerator 1000 may decrease the camera detection interval (for example, from three (3) hours to one (1) hour). The interval of image detection of the camera will be described in detail below with reference to FIGS. 17 and 18.

Meanwhile, according to an embodiment of the disclosure, when the plurality of cameras are arranged in the refrigerator 1000, each of the cameras may have a different image detection time. For example, the first camera may obtain the first camera image about the first shelf after a predetermined time period is passed after the door is opened and closed and the second camera may obtain the second camera image about the second shelf at a predetermined time interval.

According to an embodiment of the disclosure, the refrigerator 1000 may identify at least one object based on a result of analyzing the camera image. For example, the processor of the refrigerator 1000 may detect a type of the object, a name of the object, etc., by comparing an outline of the object included in the camera image with a pre-defined template. For example, when the outline of the object is similar to the template of a banana, the refrigerator 1000 may recognize the object included in the camera image as a banana.

According to an embodiment of the disclosure, the refrigerator 1000 may identify the at least one object included in the camera image by applying the camera image to an AI model for object identification. The AI model for object identification may be the same model as the AI model for predicting the state of the object or a different model from the AI model for predicting the state of the object.

In operation S220, the refrigerator 1000 may obtain environmental information in the refrigerator 1000 through an environmental sensor arranged in the refrigerator 1000.

According to an embodiment of the disclosure, the environmental sensor may include at least one of a temperature sensor, a humidity sensor, or an odor sensor, but it is not limited thereto. According to an embodiment of the disclosure, at least one of the temperature sensor, the humidity sensor, or the odor sensor may be arranged in the refrigerator 1000. In this case, each of the temperature sensor, the humidity sensor, and the odor sensor may be singularly arranged in the refrigerator 1000, or each of the temperature sensor, the humidity sensor, and the odor sensor may be arranged in the refrigerator 1000 in a multiple number. For example, a first temperature sensor, a first humidity sensor, and a first odor sensor may be arranged in a first shelf in the refrigerator 1000, a second temperature sensor, a second humidity sensor, and a second odor sensor may be arranged in a second shelf in the refrigerator 1000, and a third temperature sensor, a third humidity sensor, and a third odor sensor may be arranged in a third shelf in the refrigerator 1000.

According to an embodiment of the disclosure, the environmental information in the refrigerator 1000 may be information about an environment in the refrigerator 1000 and may include, for example, at least one of temperature information, humidity information, or odor information. The temperature information may include, but is not limited to, a current temperature around an object, an average temperature in the refrigerator 1000, and a change of a temperature during a predetermined time. The humidity information may include, but is not limited to, a current humidity around the object, an average humidity in the refrigerator 1000, and a change of a humidity during a predetermined time. The odor information may include, but is not limited to, information of the quantity of detected gas, the type of gas, and an average gas concentration in the refrigerator 1000.

Thus, the refrigerator 1000 may obtain at least one of the temperature information, the humidity information, or the odor information in the refrigerator 1000 by using at least one of the temperature sensor, the humidity sensor, or the odor sensor.

In operation S230, the refrigerator 1000 may predict information related to a current state of at least one object by applying the camera image including the at least one object and the environmental information in the refrigerator 1000 to the AI model.

According to an embodiment of the disclosure, the information related to the current state of the at least one object may include, but is not limited to, the current state of the at least one object, a consumable period (or an expected disposal time point) based on the current state, and information about a change in a state after a predetermined time period from a current point in time.

According to an embodiment of the disclosure, the current state of the at least one object may be divided into a fresh state, a ripe state, and a spoiled state, but it is not limited thereto. For example, referring to FIG. 4, when an object is well maintained according to a maintenance standard, the AI model may determine the state of the object from a manufacturing date (a shipment date) to an expiration date as a fresh state, the state of the object from the expiration date to a date on which the object starts to get spoiled as a ripe state, and the state of the object from the date on which the object starts to get spoiled as a spoiled state, but it is not limited thereto. For example, the AI model may divide the state of the object into first through tenth stages via training, and determine the state of the object in the first through fourth stages as the fresh state, the state of the object in the fifth through seventh stages as the ripe state, and the state of the object after the eighth stage as the spoiled state.

According to an embodiment of the disclosure, the refrigerator 1000 may predict the current state of the at least one object, by applying the camera image including the at least one object and the temperature information (or the humidity information) around the at least one object to the AI model. Here, the AI model may be an artificial neural network which is trained using the camera image, the temperature information (or the humidity information), and the state of the object as learning data. For example, when 10% of a skin of a banana included in the camera image is black and the temperature around the banana is 1° C., the AI model may determine the current state of the banana as the ripe state. Also, when 90% of the skin of the banana included in the camera image is black and the temperature around the banana is 2° C., the AI model may determine the current state of the banana as the spoiled state.

According to an embodiment of the disclosure, the refrigerator 1000 may predict the current state of the at least one object, by applying the camera image including the at least one object and the odor information of the at least one object to the AI model. For example, when the refrigerator 1000 applies the camera image including a tomato and the odor information (for example, the degree of odor: 150 μm and the type of odor: fatty acid odor) of the tomato to the AI model, the AI model may determine the current state of the tomato based on the camera image including the tomato and the odor information of the tomato. Here, even when the tomato is partially or totally hidden by another objet in the camera image, the AI model may predict the current state of the tomato by using the odor information of the tomato. Here, the AI model may be an artificial neural network which is trained using the camera image, the odor information, and the state of the object as learning data.

According to an embodiment of the disclosure, the refrigerator 1000 may predict the current state of the at least one object, by applying the camera image including the at least one object, the temperature information (or the humidity information) around the at least one object, and the odor information of the at least one object to the AI model. Also, the refrigerator 1000 may predict the current state of the at least one object, by applying the camera image including the at least one object, the temperature information around the at least one object, the humidity information around the at least one object, and the odor information of the at least one object to the AI model.

According to an embodiment of the disclosure, when the current state of the object is not the spoiled state, the AI model may predict a consumable period (for example, a remaining period from a current point in time to an expected disposal date) of the object. For example, the AI model may determine that the current state of the banana is the ripe state and the remaining period until the expected disposal date is three (3) days, based on the camera image including the banana and the environmental information around the banana. In this case, the AI model may transmit the information about the current state (for example, the ripe state) of the banana and the remaining period (for example, three (3) days) until the expected disposal date to the processor of the refrigerator 1000.

Meanwhile, according to an embodiment of the disclosure, the refrigerator 1000 may more accurately predict the current state of the object by further applying a spectrometric image to the AI model, in addition to the camera image and the environmental information. An operation of using the spectrometric image by the refrigerator 1000 will be described in detail below with reference to FIG. 6.

In operation S240, the refrigerator 1000 may provide the information related to the current state of the at least one object.

According to an embodiment of the disclosure, the information related to the current state of the at least one object may include at least one of the freshness of the at least one object, the ripeness of the at least one object, whether the at least one object is consumable or not, or information (for example, information about a remaining period until an expected disposal date) about a consumable period of the at least one object, but it is not limited thereto.

According to an embodiment of the disclosure, the refrigerator 1000 may provide the information about the consumable period of the at least one object based on the current state of the at least one object. For example, the refrigerator 1000 may provide the information about the consumable period of each of fresh food items (for example, a tomato, a banana, an eggplant, a carrot, a cucumber, etc.) kept in the refrigerator 1000. For example, when the tomato is not yet in the ripe state, the refrigerator 1000 may obtain, from the AI model, a result that the consumable period of the tomato is "after three (3) days until ten (10) days." Also, the refrigerator 1000 may display the consumable period (for example, 3 to 10 days) of the tomato on a display coupled to the door.

According to an embodiment of the disclosure, the refrigerator 1000 may display the information about the consumable period on the camera image including the at least one object in an overlapping manner. For example, when the camera image includes a banana, a cucumber, and an eggplant, the refrigerator 1000 may display an expected disposal date (for example, five (5) days remaining) of the banana on the image of the banana, may display an expected disposal date (for example, seven (7) days remaining) of the cucumber on the image of the cucumber, and may display "three (3) days passed after the expected disposal date" or "immediate disposal required (spoiled)" on the image of the eggplant.

Meanwhile, according to an embodiment of the disclosure, the refrigerator 1000 may display the expected disposal date in a different color according to the consumable period. For example, when the consumable period is expired (when the object is already spoiled), the refrigerator 1000 may display the expected disposal date (for example, three (3) days passed) in a red color, when the consumable period is left within two (2) days, the refrigerator 1000 may display the expected disposal date in an orange color, when the consumable period is left between three (3) days and seven (7) days, the refrigerator 1000 may display the expected disposal date in a yellow color, and when eight (8) or more days of the consumable period are left, the refrigerator 1000 may display the expected disposal date in a green color.

According to an embodiment of the disclosure, the refrigerator 1000 may display the information about the consumable periods of the objects kept in the refrigerator 1000 in the form of a list. For example, the refrigerator 1000 may provide the list of the objects by displaying the list of the objects such that the object having a shorter consumable period is displayed above.

According to an embodiment of the disclosure, the refrigerator 1000 may provide the information about the ripeness or the freshness of the at least one object. For example, when the banana is appropriately ripe, the refrigerator 1000 may provide the notification that "the banana is currently in its best state" through the display. Also, the refrigerator 1000 may briefly display the notification "spoiled," "to be spoiled soon," "consumable," "fresh," etc., on the camera image as the information about the ripeness or the freshness.

According to an embodiment of the disclosure, the refrigerator 1000 may provide the information related to the current state of the at least one object through the display of the refrigerator 1000 or the mobile terminal 3000. For example, the refrigerator 1000 may sense a user approaching the refrigerator 1000 through a camera installed outside the refrigerator 1000. Here, the refrigerator 1000 may display the information related to the current state of the objects kept in the refrigerator 1000 through a display arranged outside the refrigerator 1000. Also, when a user executes a "refrigerator application" in the mobile terminal 3000 connected with the refrigerator 1000, the mobile terminal 3000 may display the information related to the current state of the objects kept in the refrigerator 1000.

Hereinafter, the AI model for predicting the current state of the at least one object will be described in more detail with reference to FIG. 3.

Figure 3:
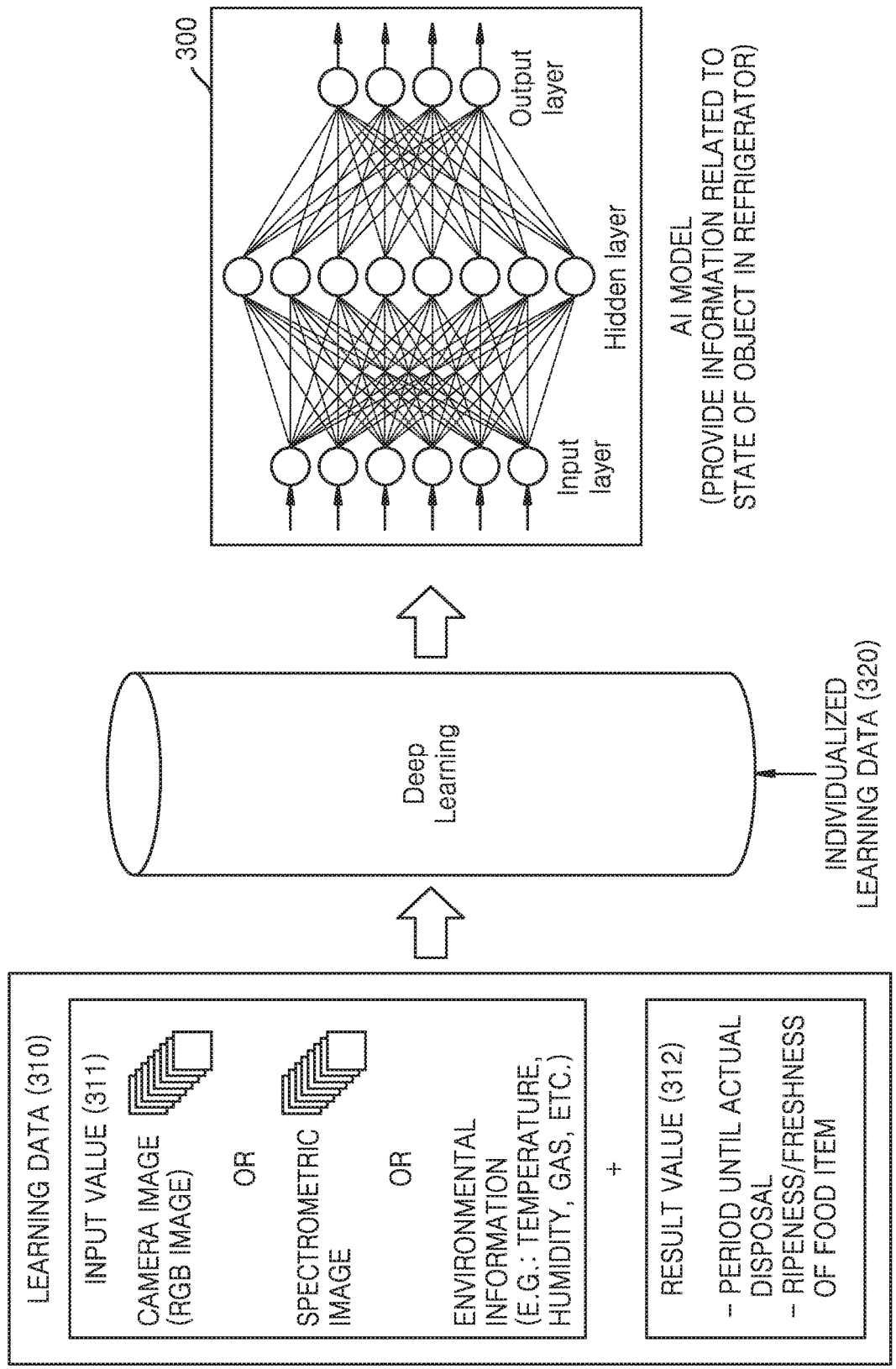
FIG. 3 is a view for describing an operation of generating an artificial intelligence (AI) model via deep learning, according to an embodiment of the disclosure.

FIG. 3 is a view for describing an operation of generating an AI model via deep learning, according to an embodiment of the disclosure.

Referring to FIG. 3, according to an embodiment of the disclosure, an AI processor included in the refrigerator 1000 or the server apparatus 2000 may train an artificial neural network and generate an AI model 300 configured to predict a current state of an object kept in the refrigerator 1000. To "train" the artificial neural network may denote to generate an arithmetic model capable of performing optimal decision making via connection of neurons included in the artificial neural network, while appropriately changing the weight based on data.

According to an embodiment of the disclosure, the AI processor may obtain a set of learning data 310 including an input value 311 and a result value 312. Here, the input value 311 may include at least one of a camera image (an RGB image), a spectrometric image, or environmental information (for example, temperature information, humidity information, and odor (gas) information) and the result value 312 may include at least one of a time until actual disposal, the ripeness of a food item, or the freshness of a food item, but it is not limited thereto.

According to an embodiment of the disclosure, the camera image obtained as the learning data 310 may include RGB images of various objects which may be kept in the refrigerator 1000. Also, the camera image may include RGB images of various states of the same object. The camera image may be a two-dimensional (2D) image or a three-dimensional (3D) image.

According to an embodiment of the disclosure, the spectrometric image obtained as the learning data 310 may include images obtained via spectrometric analysis with respect to various objects which may be kept in the refrigerator 1000. The spectrometric analysis is a technique for detecting a change of a material property in an object in a nondestructive manner. When the artificial neural network learns the spectrometric image of the object, not only a physical property of the object, but also a biochemical property of the object may be comprehensively analyzed from the spectrometric image of the object. According to an embodiment of the disclosure, the AI processor may obtain the spectrometric image of various states of the same object from the learning data 310. The spectrometric image may be a 2D image or a 3D image.

According to an embodiment of the disclosure, the environmental information obtained as the learning data 310 may be information about an environment in the refrigerator 1000 at a time point in which the camera image or the spectrometric image is detected. For example, the environmental information may include at least one of temperature information, humidity information, or odor (gas) information, but it is not limited thereto.

Figure 4:
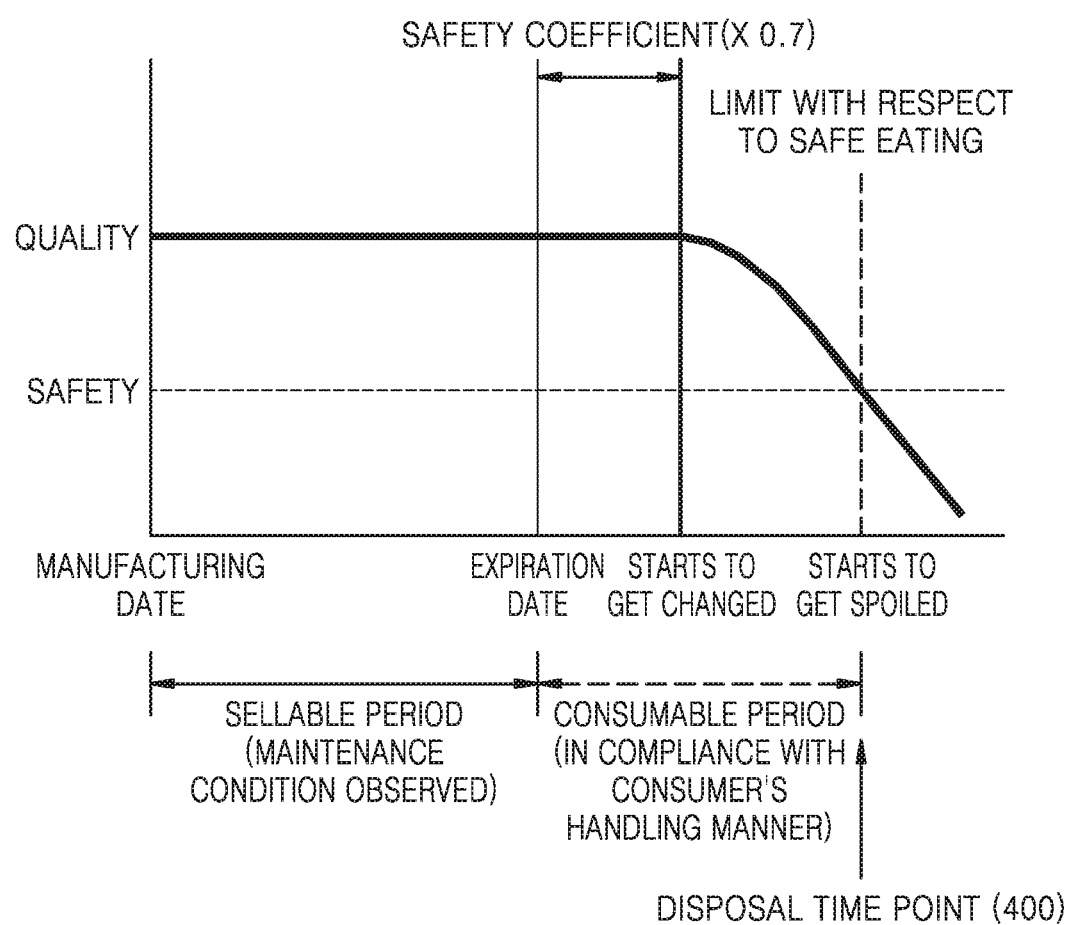
FIG. 4 is a view for describing a disposal time point according to an embodiment of the disclosure.

By referring to FIG. 4, a time period until actual disposal, which is collected as the result value 312, may be a remaining period until a time point in which an object actually starts to get spoiled (that is, a disposal time point 400). The period until actual disposal may vary according to an environment in which the object is kept, and thus, the AI model 300 is required to learn (to be trained about) the period until actual disposal with the environmental information.

According to an embodiment of the disclosure, the AI model 300 may learn (may be trained about) the camera image, the spectrometric image, or the environmental information as the input value 311 and the period until actual disposal, the ripeness of a food item, or the freshness of a food item as the result value 312. Thus, when at least one of the camera image, the spectrometric image, or the environmental information is input, the AI model 300 may predict the consumable period, the ripeness, or the freshness of the food item.

According to an embodiment of the disclosure, when the camera image, the spectrometric image, and the environmental information collected by the AI processor as the learning data are increased, the AI model 300 may be refined, and the consumable period, the ripeness, and the freshness predicted by the refined AI model 300 may have increased accuracy.

Referring to FIG. 5, the learning data 310 may include a set including a camera image 501, a spectrometric image 502, environmental information 503, and a consumable period 504. For example, the AI processor may obtain a first camera image including a first banana which is not ripe, a first spectrometric image about the first banana, a first quantity of gas detected (50 μm) in a refrigerator keeping the first banana, a first temperature (4° C.), a first humidity (40%), and a consumable period (after two (2) days until nine (9) days) of the first banana, as a first learning data set. The AI processor may obtain a second camera image including a second banana which is ripe, a second spectrometric image about the second banana, a second quantity of gas detected (125 μm) in the refrigerator keeping the second banana, a second temperature (3° C.), a second humidity (35%), and a consumable period (from a current point in time up to four (4) days) of the second banana, as a second learning data set.

The AI processor may obtain a third camera image including a ripe tangerine, a third spectrometric image about the tangerine, a third quantity of gas detected (70 μm) in the refrigerator keeping the tangerine, a third temperature (4° C.), a third humidity (21%), and a consumable period (from a current point in time up to sixteen (16) days) of the tangerine, as a third learning data set. Also, the AI processor may obtain a fourth camera image including a tomato which is not ripe, a fourth spectrometric image about the tomato, a fourth quantity of gas detected (0 μm) in the refrigerator keeping the tomato, a fourth temperature (2° C.), a fourth humidity (42%), and a consumable period (after eight (8) days up to twenty five (25) days) of the tomato, as a fourth learning data set.

According to an embodiment of the disclosure, the AI processor may generate various types of learning data sets in order to increase the accuracy of prediction of the AI model 300.

According to an embodiment of the disclosure, the AI processor may obtain individualized learning data 320. The individualized learning data 320 may include, but is not limited to, data about an environment in which an individual keeps an object, data about a type of object preferred by an individual, data about a ripeness of an object, preferred by an individual, data about a health state of an individual, etc. The AI processor may train the AI model 300 by using the individualized learning data 320.

Hereinafter, when the AI model 300 is a model having learned a spectrometric image, the operation performed by the refrigerator 1000 to further apply the spectrometric image to the AI model 300 to predict a state of at least one object will be described in detail.

Figure 6:
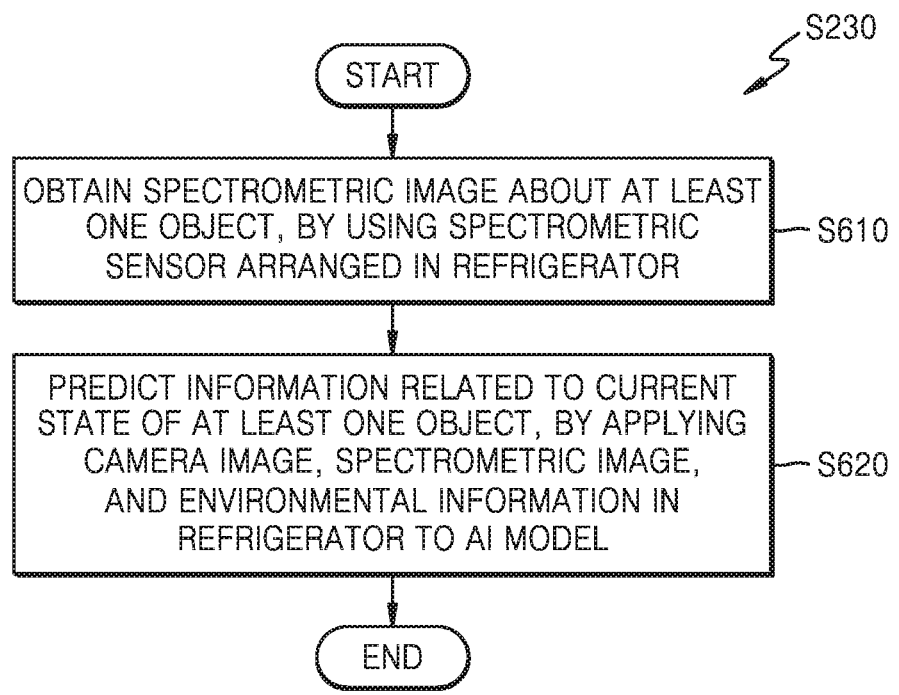
FIG. 6 is a flowchart of a method of predicting a current state of at least one object by using a spectrometric image, according to an embodiment of the disclosure.

FIG. 6 is a flowchart of a method of predicting a current state of at least one object by using a spectrometric image, according to an embodiment of the disclosure.

In operation S610, the refrigerator 1000 may obtain the spectrometric image about the at least one object by using a spectrometric sensor arranged in the refrigerator 1000.

According to an embodiment of the disclosure, the spectrometric sensor arranged in the refrigerator 1000 may obtain spectrometric information of the at least one object by irradiating light to the at least one object by selectively combining sequential wavelengths of visible rays and near-infrared rays. Here, the spectrometric sensor may analyze physical and biochemical characteristics of the at least one object through intrinsic optical characteristics of the at least one object and generate the spectrometric image, by using the spectrometric information.

According to an embodiment of the disclosure, the spectrometric sensor may be arranged around a camera in the refrigerator 1000. Also, a plurality of spectrometric sensors may be arranged in the refrigerator 1000. For example, the spectrometric sensors may include a first spectrometric sensor to obtain a spectrometric image of first objects kept in a first shelf, a second spectrometric sensor to obtain a spectrometric image of second objects kept in a second shelf, a third spectrometric sensor to obtain a spectrometric image of third objects kept in a third shelf, etc., but it is not limited thereto.

According to an embodiment of the disclosure, the refrigerator 1000 may obtain the spectrometric image by using the spectrometric sensor after a predetermined time period after a user opens and closes a door of the refrigerator 1000 (for example, after three (3) seconds after the door of the refrigerator 1000 is closed). In this case, because the objects kept in the refrigerator 1000 may be changed because the user opens and closes the door, the refrigerator 1000 may obtain the spectrometric image of the changed objects in real time.

According to an embodiment of the disclosure, the refrigerator 1000 may obtain the spectrometric image by using the spectrometric sensor at a predetermined time interval. For example, the refrigerator 1000 may obtain the spectrometric image by using the spectrometric sensor at an interval of three (3) hours.

According to an embodiment of the disclosure, an interval at which the spectrometric sensor detects the spectrometric image may be synchronized with an interval at which a camera detects an image. For example, when the image detection interval of the camera is one (1) hour, a processor of the refrigerator 1000 may adjust the spectrometric image detection interval of the spectrometric sensor as one (1) hour.

According to an embodiment of the disclosure, the spectrometric sensor may obtain the spectrometric image of a specific object by irradiating light to the specific object. For example, the spectrometric sensor may obtain the spectrometric image of a first object by irradiating light to the first object having a gas detection quantity, which is greater than a critical value.

In operation S620, the refrigerator 1000 may predict the information related to the current state of the at least one object by applying the camera image, the spectrometric image, and the environmental information in the refrigerator 1000 to the AI model 300.

Here, the AI model 300 may be an artificial neural network which is trained using the camera image, the spectrometric image, the environmental information (for example, temperature information, humidity information, or odor information), and the state of the object as learning data.

According to an embodiment of the disclosure, the refrigerator 1000 may predict the current state of the at least one object, a consumable period (or an expected disposal time) based on the current state, information about a change in the state after a predetermined time after a current point in time, etc., but it is not limited thereto.

According to an embodiment of the disclosure, the current state of the at least one object may be divided into a fresh state, a ripe state, and a spoiled state, but it is not limited thereto.

According to an embodiment of the disclosure, the AI model 300 may predict the consumable period (for example, a remaining period from a current point in time until an expected disposal date) of the object. For example, the AI model 300 may determine that the current state of a banana is a ripe state and the remaining period until the expected disposal date is three (3) days, based on the camera image including the banana, the spectrometric image about the banana, and the environmental information around the banana. In this case, the AI model 300 may transmit the information about the current state (for example, the ripe state) of the banana and the remaining period (for example, three (3) days) until the expected disposal date to the processor of the refrigerator 1000.

Hereinafter, an operation, performed by the AI model 300, of outputting the information related to the current state of the object will be described with reference to FIGS. 7 and 8.

Figure 7:
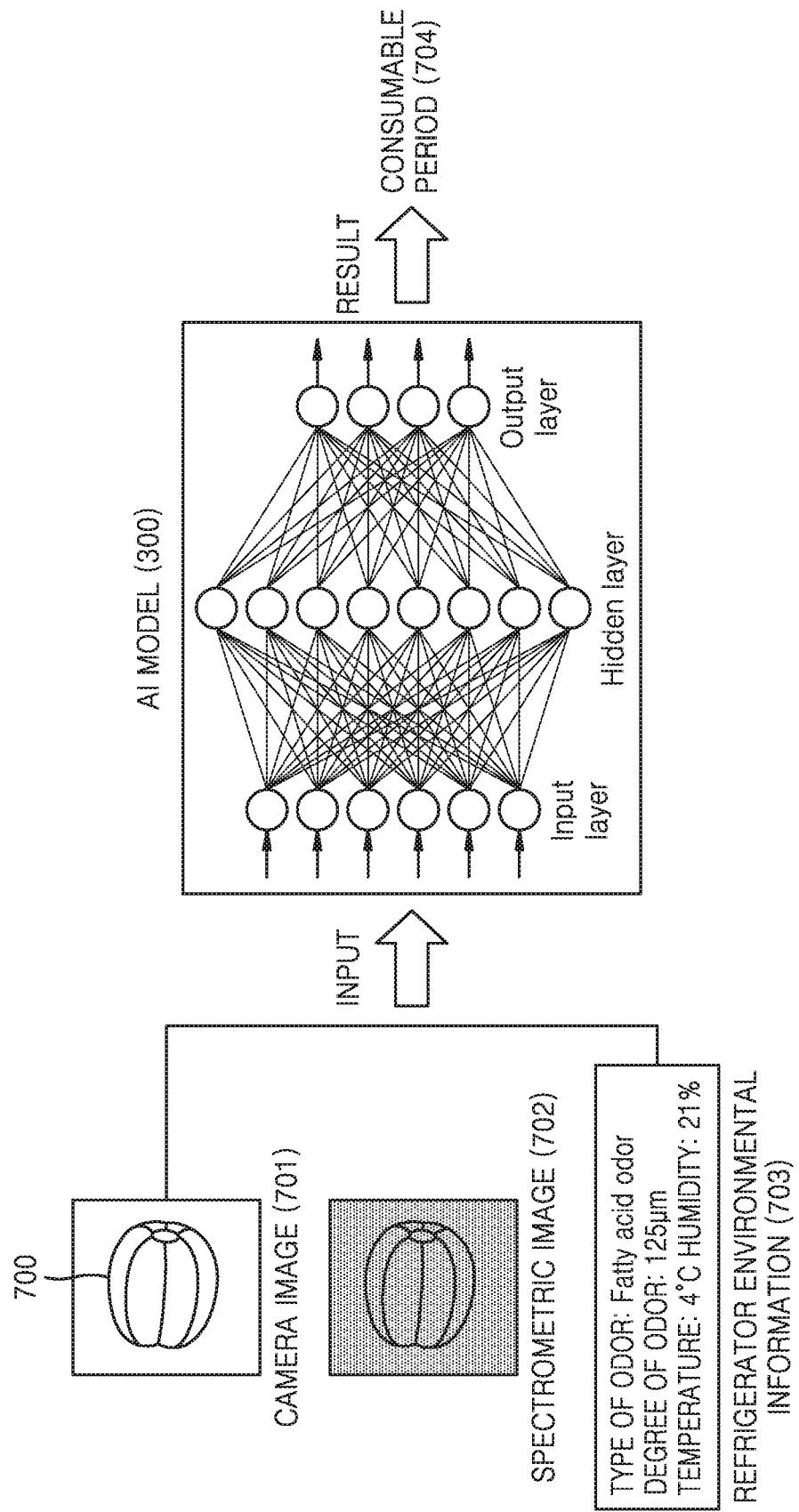
FIG. 7 is a view for describing an operation, performed by a refrigerator, of predicting a consumable period of an object by using an AI model, according to an embodiment of the disclosure.

FIG. 7 is a view for describing an operation, performed by the refrigerator 1000, of predicting a consumable period of an object by using the AI model 300, according to an embodiment of the disclosure.

Referring to FIG. 7, the refrigerator 1000 may obtain a camera image 701 about an oriental melon 700 stored in the refrigerator 1000 by using a camera, obtain a spectrometric image 702 of the oriental melon 700 by using a spectrometric sensor, and obtain refrigerator environmental information 703 (for example, the type of an odor: a fatty acid odor, the degree of an odor: 125 μm, the temperature: 4° C., and the humidity: 21%) around the oriental melon 700 by using an environmental sensor. Here, the refrigerator 1000 may input the camera image 701, the spectrometric image 702, and the refrigerator environmental information 703 into the AI model 300. The AI model 300 may generate the current state (for example, a consumable state) of the oriental melon 700 and a consumable period 704 of the oriental melon 700 as result values, based on the camera image 701, the spectrometric image 702, and the refrigerator environmental information 703.

Figure 8:
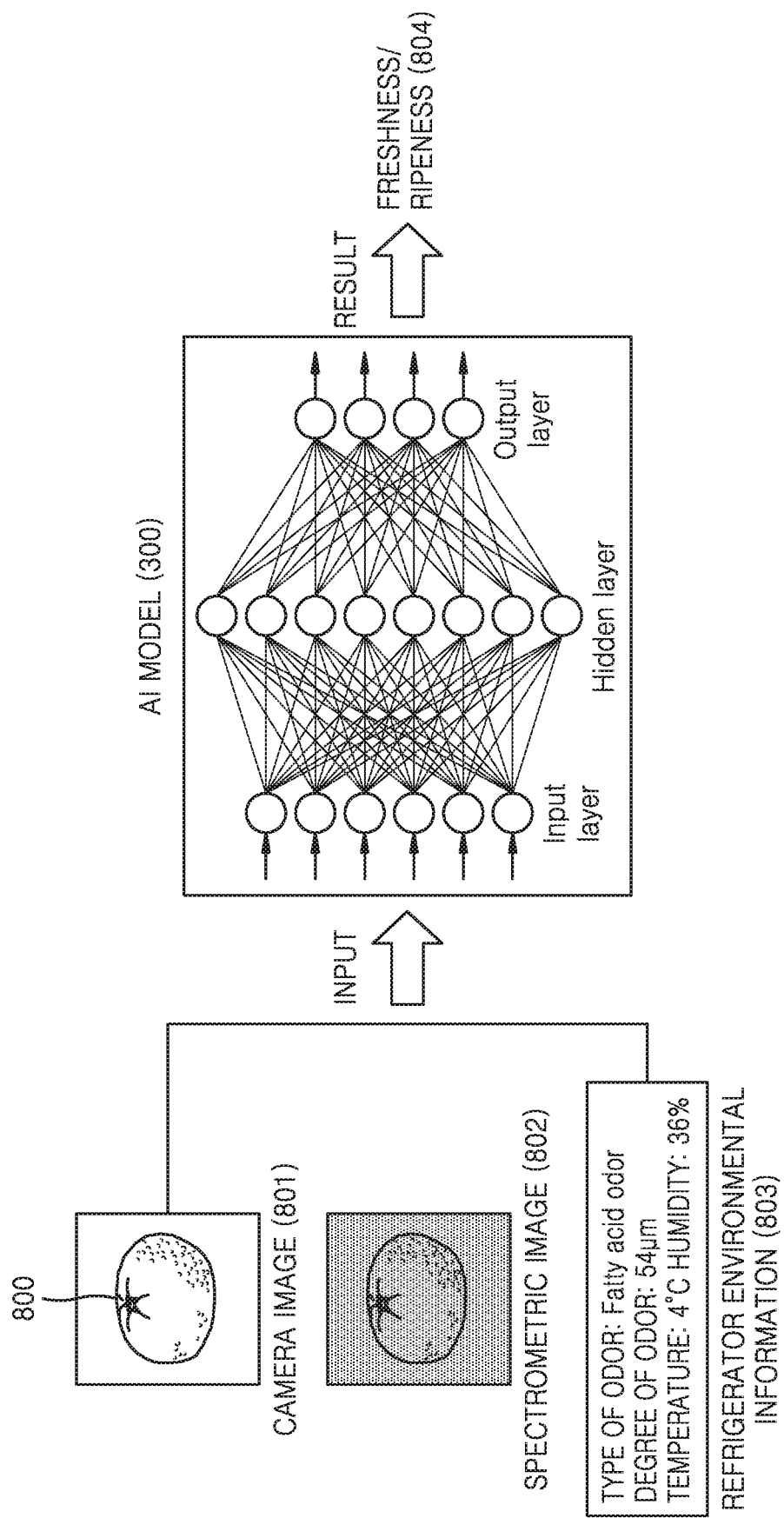
FIG. 8 is a view for describing an operation, performed by a refrigerator, of predicting a freshness or a ripeness of an object by using an AI model, according to an embodiment of the disclosure.

FIG. 8 is a view for describing an operation, performed by the refrigerator 1000, of predicting the freshness or the ripeness of an object by using the AI model 300, according to an embodiment of the disclosure.

Referring to FIG. 8, the refrigerator 1000 may obtain a camera image 801 about a tangerine 800 stored in the refrigerator 1000 by using a camera, obtain a spectrometric image 802 of the tangerine 800 by using a spectrometric sensor, and obtain refrigerator environmental information 803 (for example, the type of an odor: a fatty acid odor, the degree of an odor: 54 μm, the temperature: 4° C., and the humidity: 36%) around the tangerine 800 by using an environmental sensor. Here, the refrigerator 1000 may input the camera image 801, the spectrometric image 802, and the refrigerator environmental information 803 into the AI model 300. The AI model 300 may generate the current state (for example, a consumable state), the freshness/ripeness 804 (for example, the freshness: level 4 and the ripeness: level 8), etc. of the tangerine 800 as output values, based on the camera image 801, the spectrometric image 802, and the refrigerator environmental information 803.

FIGS. 7 and 8 describe the examples in which the refrigerator 1000 inputs the camera image, the spectrometric image, the type of the odor, the degree of the odor, the temperature, and the humidity into the AI model 300, but it is not limited thereto. For example, the refrigerator 1000 may input the image and the temperature into the AI model 300, input the camera image and the humidity into the AI model 300, input the camera image, the type of the odor, and the degree of the odor into the AI model 300, or input the camera image and the spectrometric image into the AI model 300.

Figure 9:
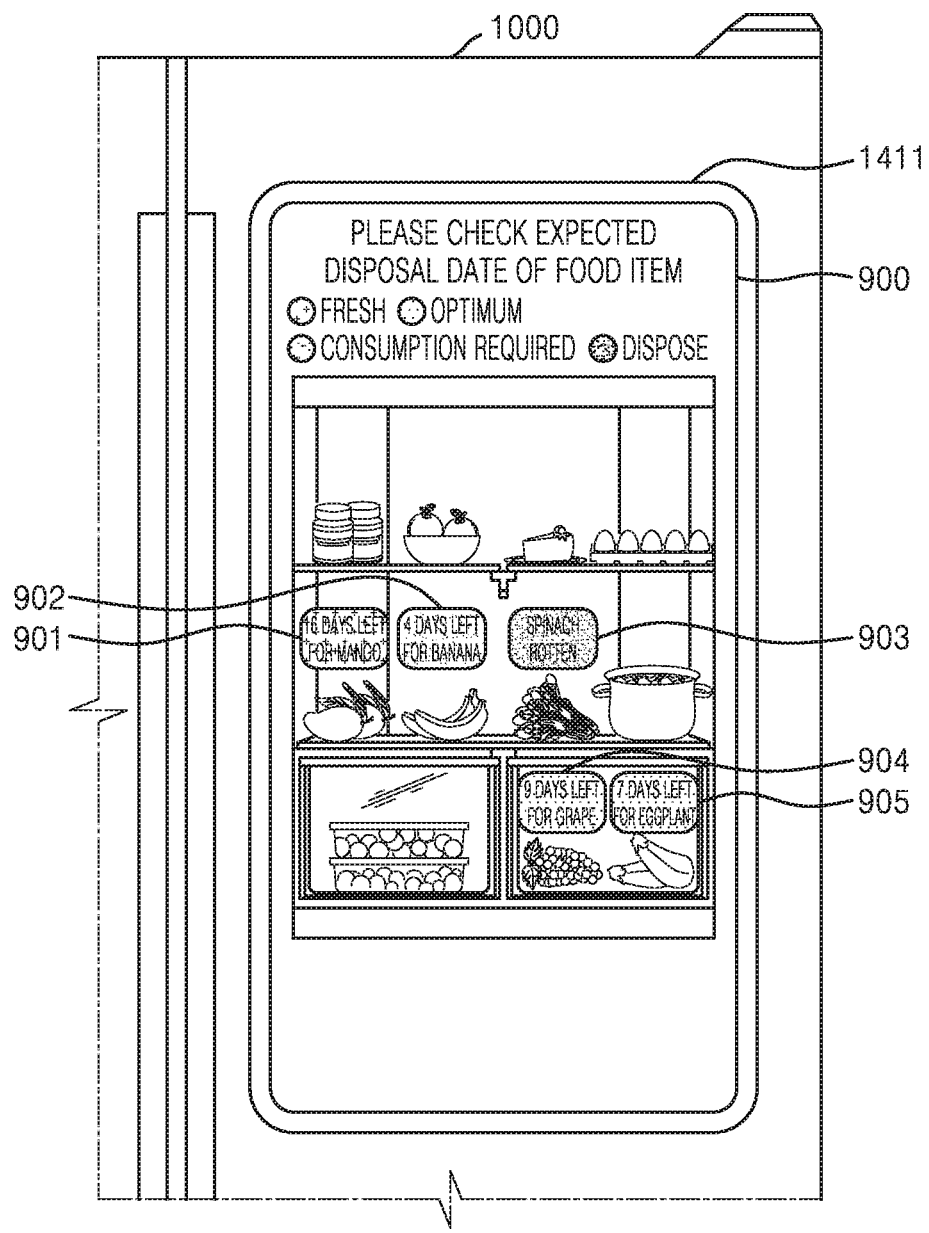
FIGS. 9 and 10 are views for describing an operation, performed by a refrigerator, of providing information about a consumable period of at least one object, according to an embodiment of the disclosure.
Figure 10:
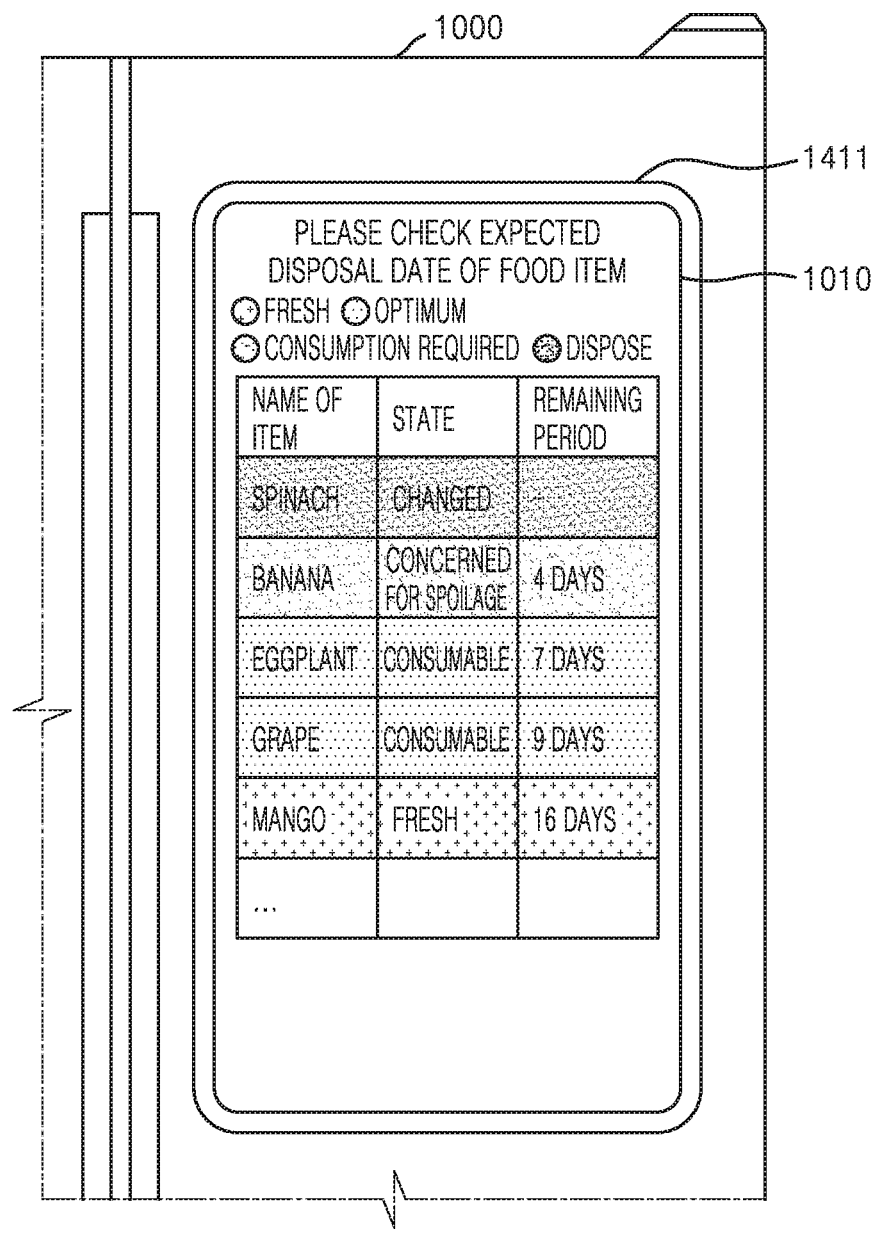

FIGS. 9 and 10 are views for describing an operation, performed by the refrigerator 1000, of providing information about a consumable period of at least one object, according to an embodiment of the disclosure.

Referring to FIG. 9, the refrigerator 1000 may provide a graphical user interface (GUI) 900 displaying notification information about consumable periods of objects stored in the refrigerator 1000, via a display 1411 arranged on a door of the refrigerator 1000. According to an embodiment of the disclosure, the refrigerator 1000 may analyze camera images of the objects stored in the refrigerator 1000, identify the objects, and display an expected disposal date of each of the objects on each of the camera images. For example, the refrigerator 1000 may display "sixteen (16) days left for mango" 901 around an image of a mango, display "four (4) days left for banana" 902 around an image of a banana, display "spinach rotten" 903 around an image of spinach, display "nine (9) days left for grape" 904 around an image of a grape, and display "seven (7) days left for eggplant" 905 around an image of an eggplant.

Meanwhile, according to an embodiment of the disclosure, a text or a mark indicating an expected disposal date may be displayed in various colors according to a remaining period until the expected disposal date. For example, the refrigerator 1000 may display the mark "spinach rotten" 903 around the image of the spinach in red, the mark "four (4) days left for banana" 902 in orange, the mark "nine (9) days left for grape" 904 and the mark "seven (7) days left for eggplant" 905 in yellow, and the mark "sixteen (16) days left for mango" 901 in green, but it is not limited thereto.

According to an embodiment of the disclosure, a user may quickly and intuitively identify which food item requires to be readily consumed via the GUI 900 displayed on the display 1411 of the refrigerator 1000. Also, the usability of the objects kept in the refrigerator 1000 may be improved and the environment in the refrigerator 1000 may be kept clean.

Referring to FIG. 10, the refrigerator 1000 may display, via the display 1411 arranged on the door of the refrigerator 1000, an object list 1010 including consumable periods (for example, remaining periods until expected disposal dates) of objects stored in the refrigerator 1000. Here, the object list 1010 may include, but is not limited to, identification information (for example, names of the objects, images of the objects, icons of the objects, etc.) of the objects, states of the objects, the remaining periods until the expected disposal dates.

Meanwhile, according to an embodiment of the disclosure, the object list 1010 may be displayed in an order of the periods remaining until the expected disposal dates, from the shortest period to longest. For example, when the spinach is spoiled, the banana has four (4) days left before the expected disposal date, the eggplant has seven (7) days left before the expected disposal date, the grape has nine (9) days left before the expected disposal date, and the mango has sixteen (16) days left before the expected disposal date, the object list 1010 may be displayed in the order of "spinach-rotten," "banana-concern for spoilage-four (4) days," "eggplant-consumable-seven (7) days," "grape-consumable-nine (9) days," and "mango-fresh-sixteen (16) days."

According to an embodiment of the disclosure, the objects may be displayed in the object list 1010 in various colors according to the remaining period until the expected disposal date. For example, the spinach may be displayed in a red background, the banana may be displayed in an orange background, the eggplant and the grape may be displayed in a yellow background, and the mango may be displayed in a green background.

Figure 11:
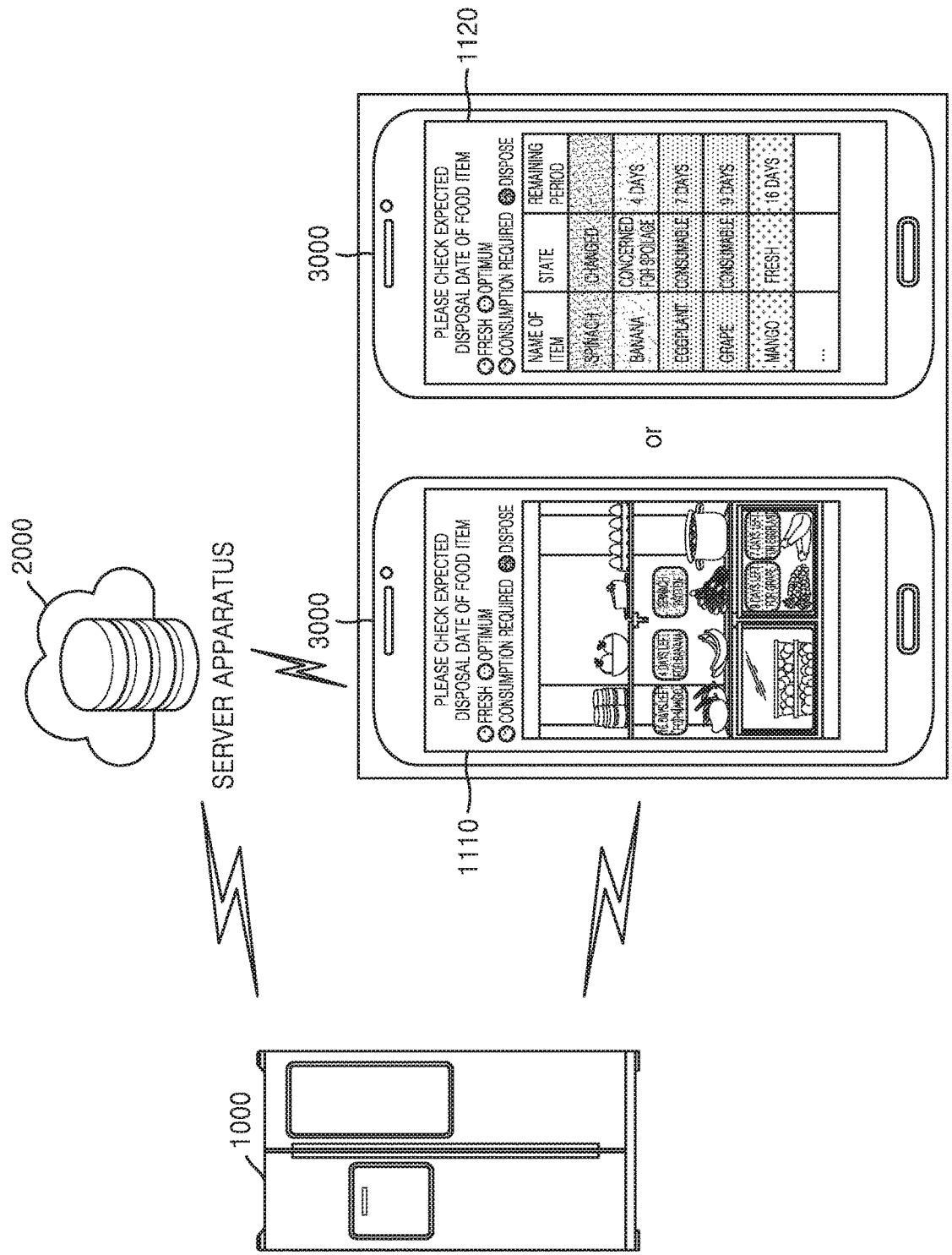
FIG. 11 is a view for describing an operation, performed by a refrigerator, of providing information about a consumable period of at least one object through a mobile terminal, according to an embodiment of the disclosure.

FIG. 11 is a view for describing an operation, performed by the refrigerator 1000, of providing information about a consumable period of at least one object through the mobile terminal 3000, according to an embodiment of the disclosure.

According to an embodiment of the disclosure, the mobile terminal 3000 may obtain information about current states and/or consumable periods of objects kept in the refrigerator 1000 from the refrigerator 1000 or the server apparatus 2000 and display the information.

According to an embodiment of the disclosure, when a user executes a refrigerator application, the mobile terminal 3000 may provide a first GUI 1110 or a second GUI 1120 via an execution window of the refrigerator application.

Referring to the first GUI 1110, the mobile terminal 3000 may display the expected disposal date of each of the objects kept in the refrigerator 1000, on the camera image of each of the objects. Here, according to an embodiment of the disclosure, a text or a mark indicating the expected disposal date may be displayed in various colors according to a remaining period until the expected disposal date.

Referring to the second GUI 1120, an object list including the consumable periods (for example, remaining periods until the expected disposal dates) of the objects kept in the refrigerator 1000 may be displayed. Here, the object list may include identification information (for example, names of the objects, images of the objects, icons of the objects, etc.) of the objects, states of the objects, and the remaining periods until the expected disposal dates, but it is not limited thereto.

Figure 12:
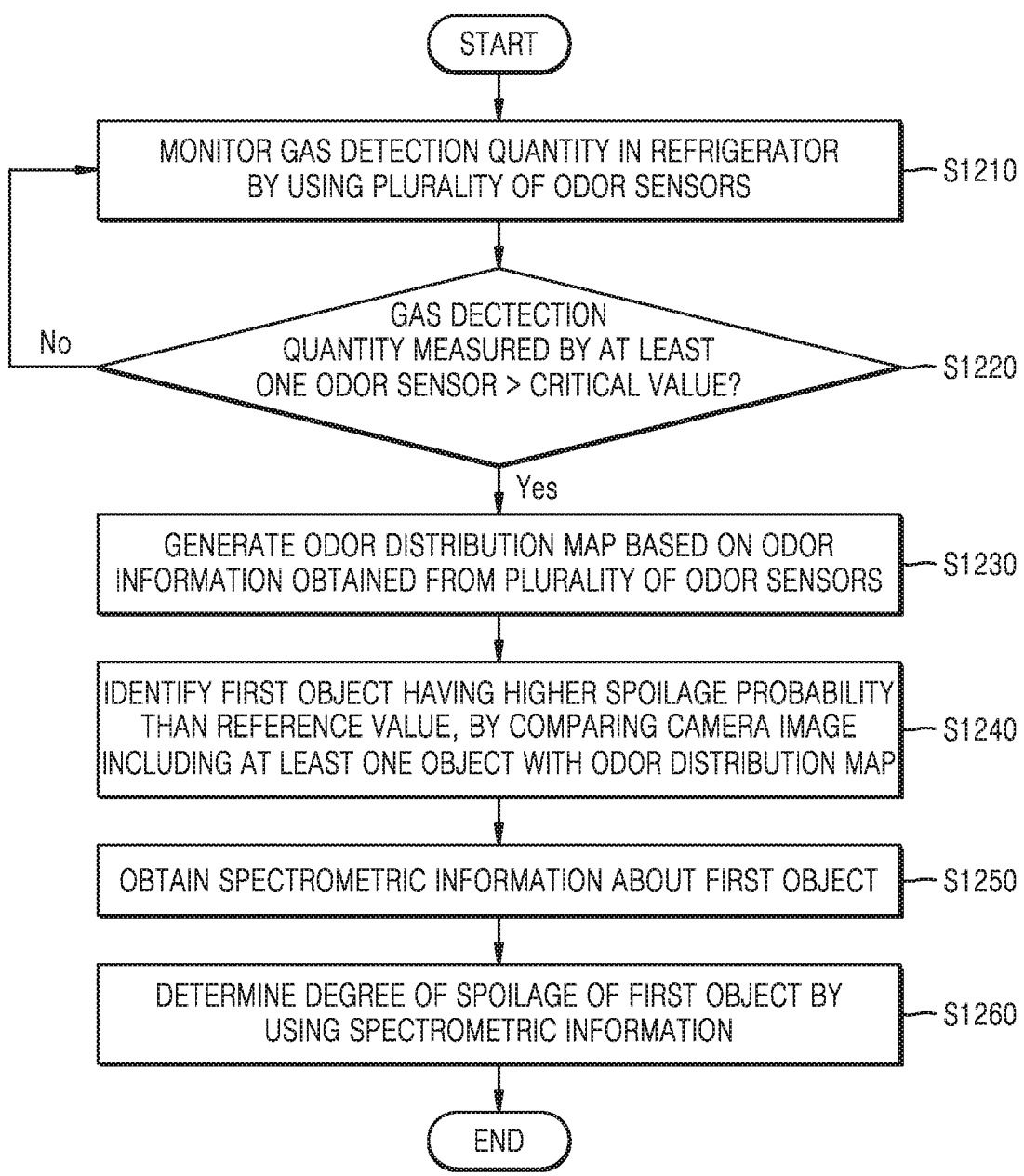
FIG. 12 is a flowchart of a method of predicting a current state of at least one object by using odor information and spectrometric information, according to an embodiment of the disclosure.

FIG. 12 is a flowchart of a method of predicting a current state of at least one object by using odor information and spectrometric information, according to an embodiment of the disclosure.

In operation S1210, the refrigerator 1000 may monitor a gas detection quantity in the refrigerator 1000 by using a plurality of odor sensors. The plurality of odor sensors may be arranged in various places in the refrigerator 1000.

In operation S1220, the refrigerator 1000 may determine whether a gas detection quantity measured by at least one odor sensor from among the plurality of odor sensors is greater than a critical value (for example, 100 μm).

According to an embodiment of the disclosure, the refrigerator 1000 may analyze odor information (for example, the gas detection quantity, the type of gas, etc.) received from the plurality of odor sensors and identify the odor sensor measuring the gas detection quantity which is greater than the critical value from among the plurality of odor sensors. Also, according to an embodiment of the disclosure, the refrigerator 1000 may detect a location of the odor sensor measuring the gas detection quantity which is greater than the critical value.

Meanwhile, when there is no odor sensor measuring the gas detection quantity which is greater than the critical value, the refrigerator 1000 may keep monitoring the gas detection quantity in the refrigerator 1000 by using the plurality of odor sensors.

In operation S1230, the refrigerator 1000 may generate an odor distribution map based on the odor information obtained from the plurality of odor sensors, when the gas detection quantity is greater than the critical value.

The odor distribution map visualizes the odor distribution in the refrigerator 1000 and may display the location of the odor, the intensity of the odor, the type of the odor, etc. For example, the odor distribution map may differently display the color, the brightness, or the extent of an odor distribution area according to the gas detection quantity. Also, the odor distribution map may differently display the color of the odor distribution area according to the type of the odor.

According to an embodiment of the disclosure, the odor distribution map may be a 2D map or a 3D map, but it is not limited thereto. For example, when there are a plurality of shelves in the refrigerator 1000, the refrigerator 1000 may generate a 2D odor distribution map for each shelf and may generate one 3D odor distribution map for the whole space in the refrigerator 1000.

In operation S1240, the refrigerator 1000 may compare a camera image including the at least one object with the odor distribution map and may identify a first object having a spoilage probability, which is greater than a reference value.

Figure 13:
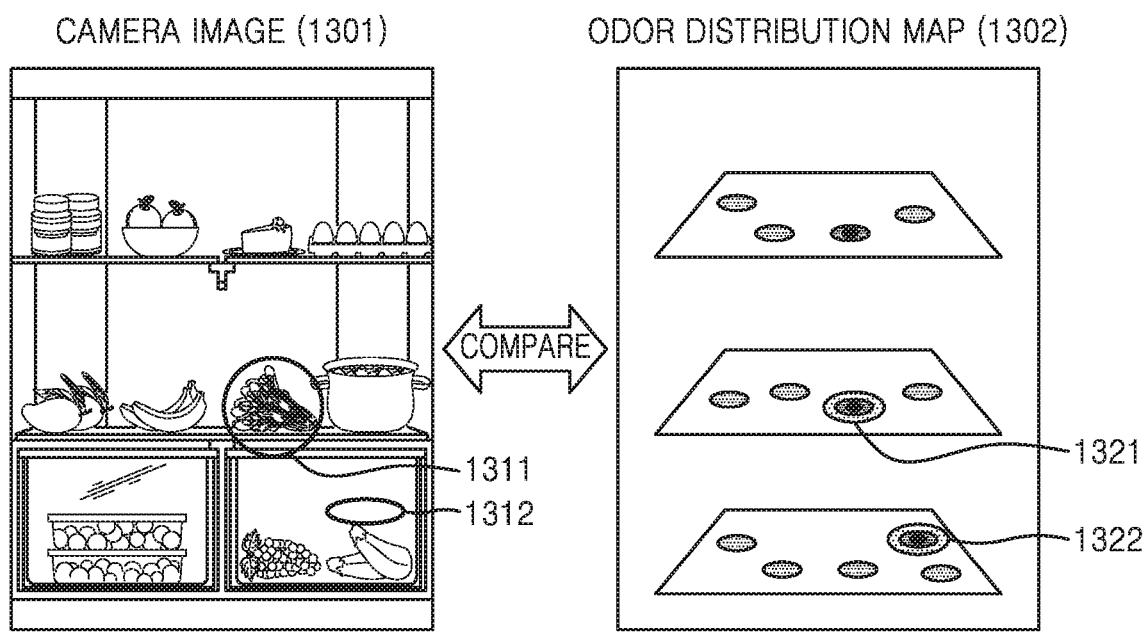
FIG. 13 is a view for describing an operation of comparing a camera image and an odor distribution map, according to an embodiment of the disclosure.

For example, referring to FIG. 13, the refrigerator 1000 may obtain a camera image 1301 about the objects stored in the refrigerator 1000 and generate an odor distribution map 1302 about the odor distribution in the refrigerator 1000. Here, the refrigerator 1000 may determine that there is an object having a high spoilage probability in a first area 1321 and a second area 1322 displayed with great extent in a dark color on the odor distribution map 1302. The refrigerator 1000 may compare the odor distribution map 1302 with the camera image 1301 and determine that "spinach" located in the first area 1311 on the camera image 1301 and an object located in the second area 1312 on the camera image 1301 have a high probability of spoilage. However, the object located in the second area 1312 is hidden by an eggplant on the camera image 1301, and thus, the refrigerator 1000 may have difficulty accurately identifying the object. Hereinafter, an example in which the first object is spinach will be described.

Referring to FIG. 12 again, in operation S1250, the refrigerator 1000 may obtain spectrometric information about the first object by using a spectrometric sensor arranged in the refrigerator 1000.

The spectrometric information about the first object may be obtained by irradiating light onto the first object by using the spectrometric sensor. The spectrometric information may include a spectrum pattern and which wavelength has a great object reflectivity may be identified based on the spectrometric information.

In operation S1260, the refrigerator 1000 may determine a degree of spoilage of the first object by using the spectrometric information about the first object.

Figure 14:
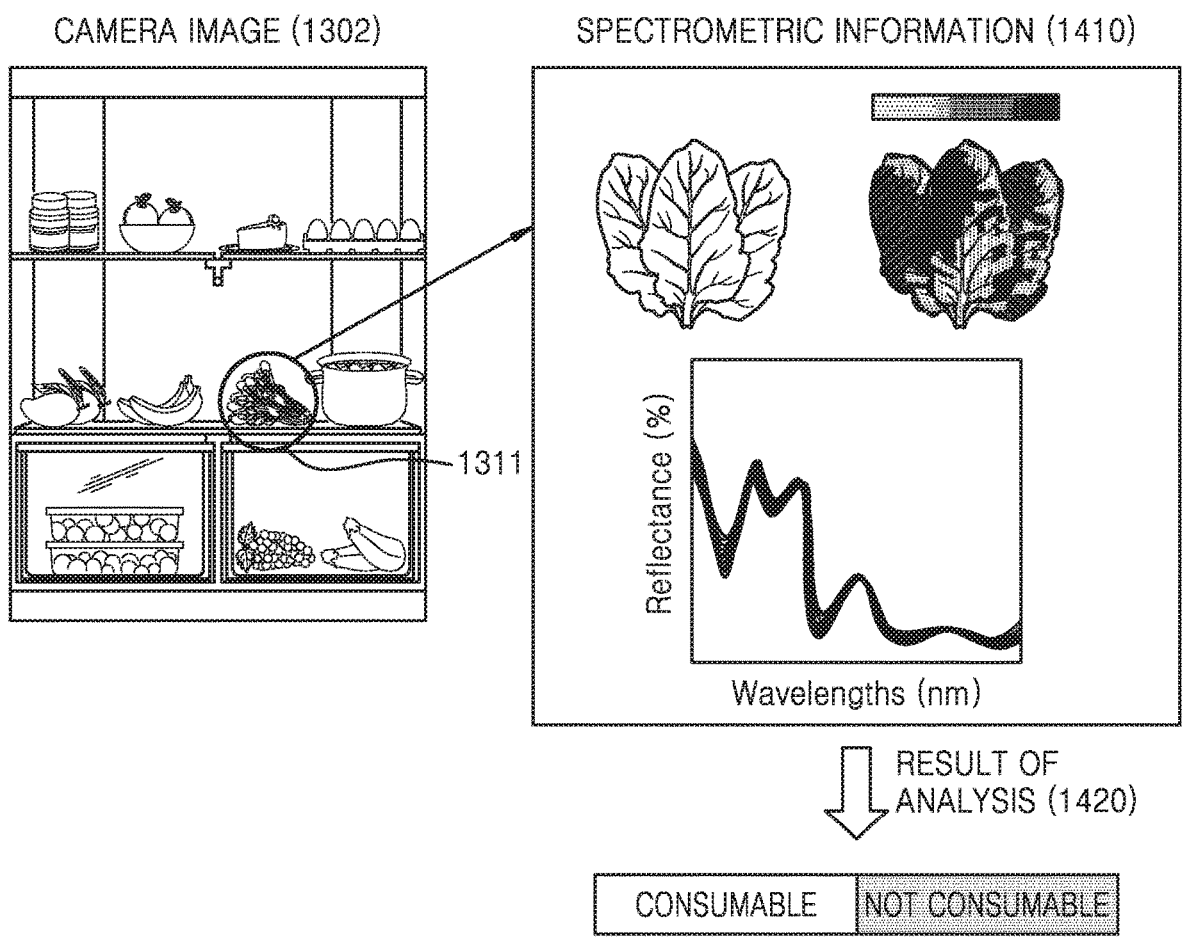
FIG. 14 is a view for describing an operation, performed by a processor of a refrigerator, of determining a degree of spoilage of a first object based on spectrometric information, according to an embodiment of the disclosure.

For example, referring to FIG. 14, the refrigerator 1000 may determine that the spinach located in the first area 1311 on the camera image 1301 has a high probability of spoilage and may irradiate light onto the spinach by using the spectrometric sensor. Also, the refrigerator 1000 may obtain spectrometric information 1410 of the spinach via the spectrometric sensor. The refrigerator 1000 may apply the spectrometric information 1410 of the spinach to the AI model 300. Here, the AI model 300 may identify a degree of spoilage (for example, the degree of spoilage: 98%) of the spinach by analyzing the spectrometric information 1410 of the spinach. The AI model 300 may transmit the degree of spoilage of the spinach to a processor of the refrigerator 1000, based on a result 1420 of analyzing the spectrometric information 1410 of the spinach.

According to an embodiment of the disclosure, the AI model 300 may determine whether the spinach is consumable or not based on the result 1420 of the analyzing the spectrometric information 1410. For example, when the spectrometric spectrum pattern of the spinach is similar to a spectrometric spectrum pattern of spinach that is not consumable, the AI model 300 may determine that the spinach is not consumable. In this case, the AI model 300 may also transmit information on whether the spinach is consumable or not to the processor of the refrigerator 1000 based on the result 1420 of the analyzing the spectrometric information 1410 of the spinach.

When the first object is not consumable according to the degree of spoilage of the first object, the refrigerator 1000 may display an attention message for consumption of the first object through the display 1411. An operation of displaying the attention message by the refrigerator 1000 will be described in detail with reference to FIG. 15.

Figure 15:
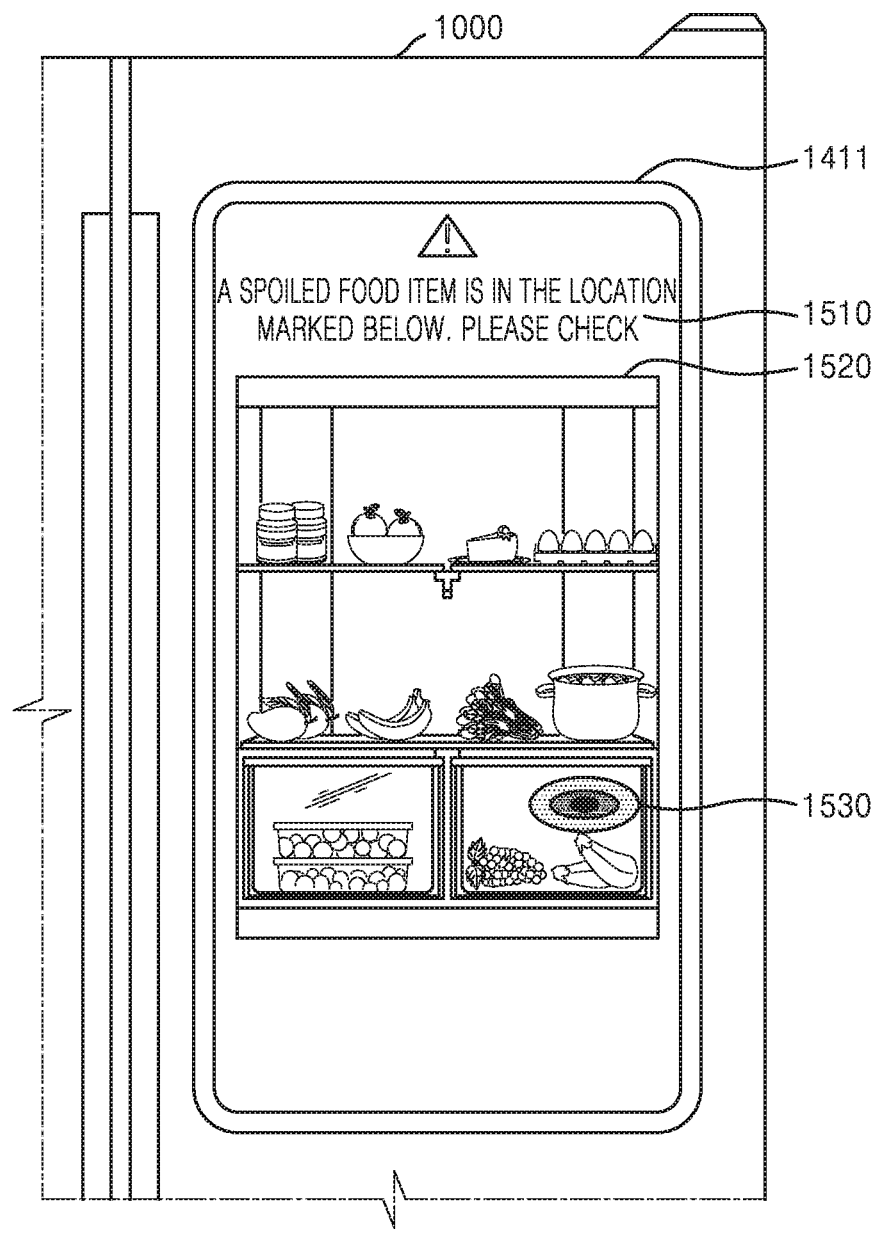
FIG. 15 is a view for describing an operation, performed by a processor of a refrigerator, of providing notification information about a position of a spoiled food item, according to an embodiment of the disclosure.

FIG. 15 is a view for describing an operation, performed by a processor of the refrigerator 1000, of providing notification information about a location of a spoiled food item, according to an embodiment of the disclosure.

According to an embodiment of the disclosure, when the first object determined as not consumable is partly or entirely hidden by a second object on the camera image, the refrigerator 1000 may provide notification information about a location in the refrigerator 1000, in which the first object is stored. For example, referring to FIG. 13, when strawberries located in the second area 1312 on the camera image 1301 are hidden by an eggplant and not seen and it is determined that the strawberries are not consumable based on the odor information, the refrigerator 1000 may provide the notification information about the second area 1312 in which the strawberries are stored to a user.

Referring to FIG. 15, the refrigerator 1000 may display, via the display 1411, a camera image 1520 in which an identification mark 1530 is added to the second area 1312 in which the strawberries are kept, together with an attention comment 1510 (for example, there is a spoiled food item at a location marked below. Please check).

Figure 16:
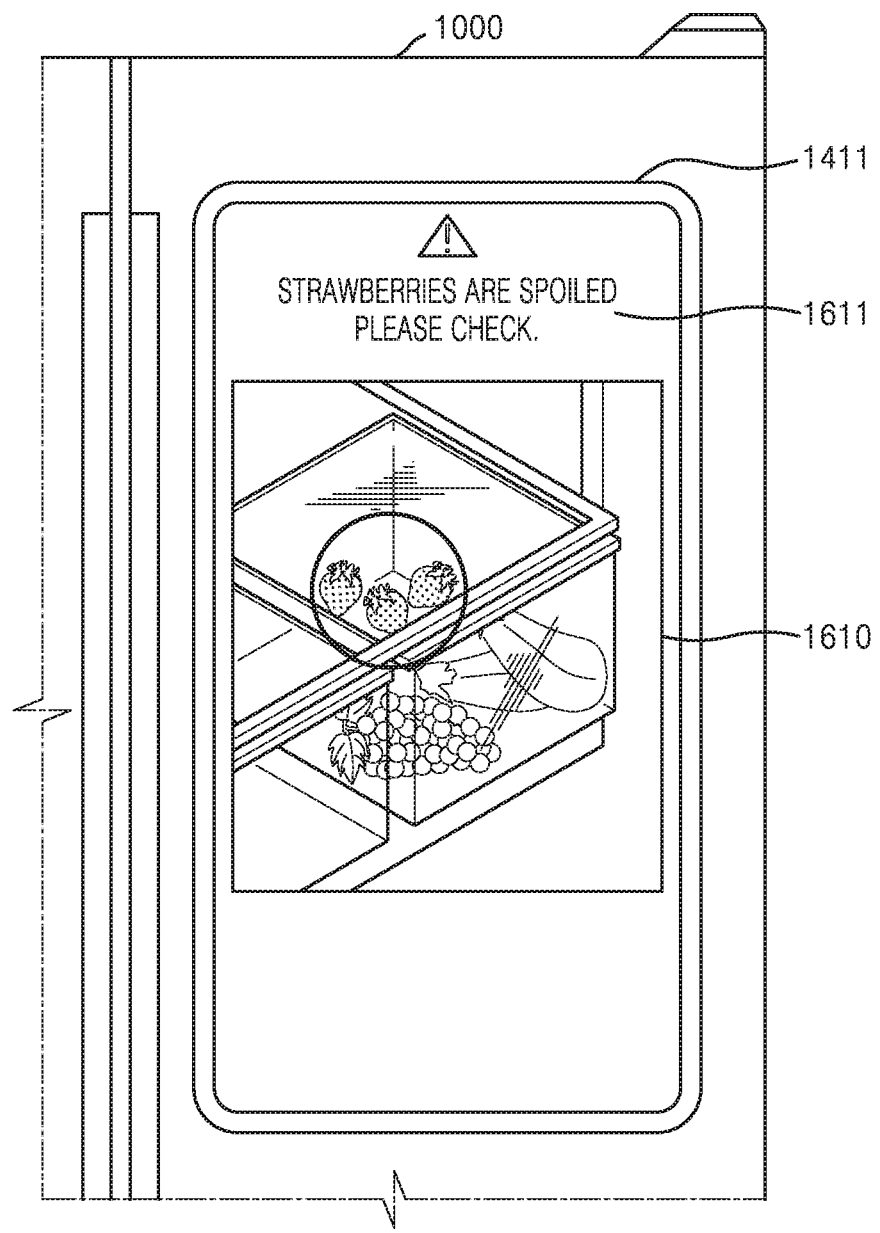
FIG. 16 is a view for describing an operation, performed by a processor of a refrigerator, of controlling a position of a camera to face toward a spoiled food item, according to an embodiment of the disclosure.

FIG. 16 is a view for describing an operation, performed by a processor of the refrigerator 1000, of controlling a position of a camera such that the camera faces toward a spoiled food item, according to an embodiment of the disclosure.

According to an embodiment of the disclosure, when a first object determined as not consumable is partly or entirely hidden by a second object in a camera image, the processor of the refrigerator 1000 may control the position of the camera such that the camera is able to capture the first object. For example, when the first object included in a first shelf is not captured by a first camera capturing a front surface of the first shelf, the refrigerator 1000 may control a second camera arranged above the first camera to be toward a bottom portion so that the second camera may capture the first object kept in the first shelf.

Referring to FIG. 16, the refrigerator 1000 may analyze a camera image 1610 obtained by the second camera, may identify that the first object determined as not consumable is strawberries, and may display a location of the strawberries on the camera image 1610. Also, the refrigerator 1000 may display an attention comment 1611, such as "strawberries are spoiled, please check."

Figure 17:
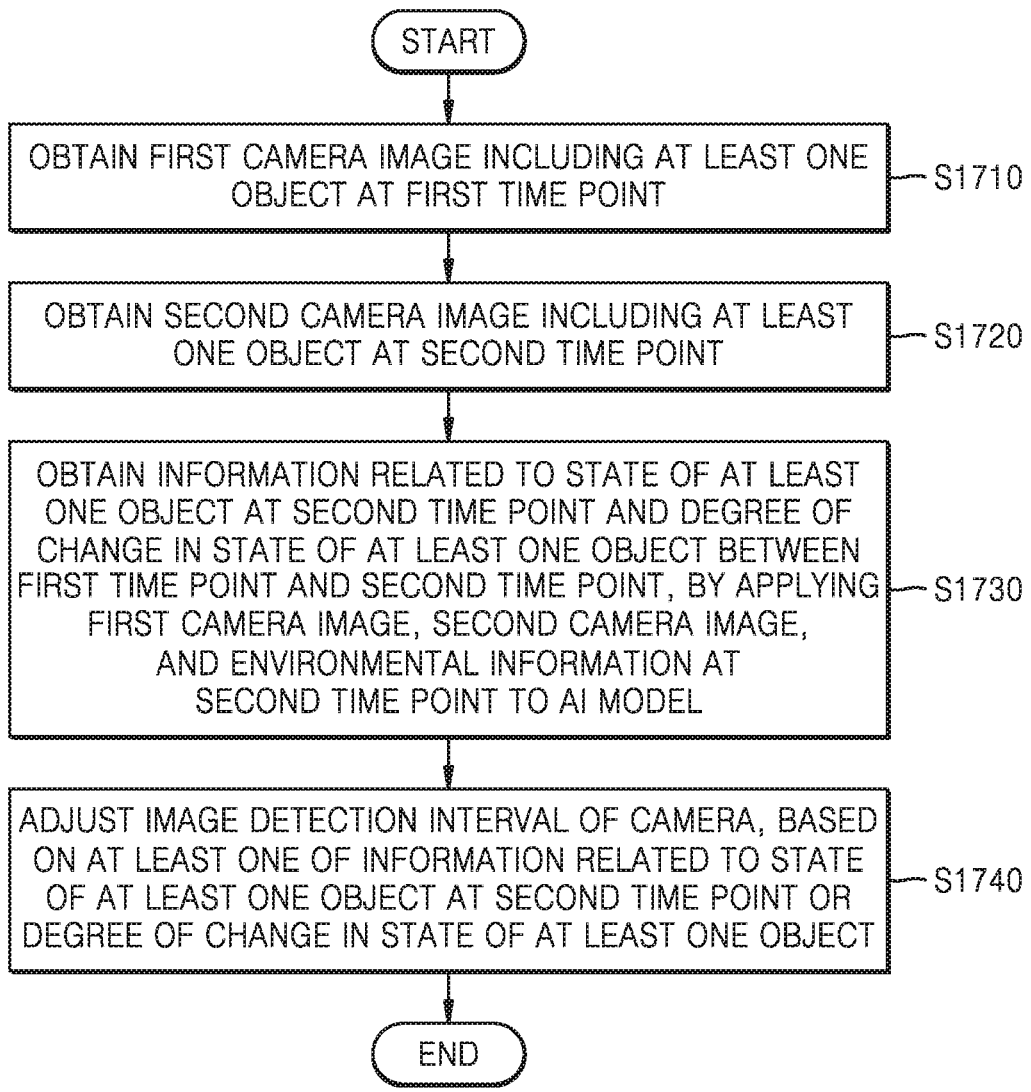
FIG. 17 is a flowchart of a method of controlling an interval of image detection of a camera, according to an embodiment of the disclosure.

FIG. 17 is a flowchart of a method of adjusting an image detection interval of a camera, according to an embodiment of the disclosure.

In operation S1710, the refrigerator 1000 may obtain a first camera image including at least one object at a first time point. The first camera image may be an RGB image. The first camera image may include one object or a plurality of objects.

In operation S1720, the refrigerator 1000 may obtain a second camera image including the at least one object at a second time point. Here, the second time point may be a time point after the first time point. Meanwhile, the first camera image and the second camera image are images captured by the same camera and may include the same object.

In operation S1730, the refrigerator 1000 may obtain information related to a state of the at least one object at the second time point and a degree of a change in the state of the at least one object between the first time point and the second time point, by applying the first camera image, the second camera image, and environmental information at the second time point to the AI model 300.

According to an embodiment of the disclosure, the refrigerator 1000 may identify the degree of the change in the state (for example, the ripeness is changed from 10% to 80%) of an object (hereinafter, referred to as a common object) commonly included in the first camera image and the second camera image, by applying the first camera image obtained at the first time point and the second camera image obtained at the second time point to the AI model 300.

Also, according to an embodiment of the disclosure, the refrigerator 1000 may obtain information related to a state of the common object at the second time point, by applying the second camera image and the environmental information (for example, temperature information, humidity information, or odor information) at the second time point to the AI model 300. According to an embodiment of the disclosure, the information related to the state of the common object at the second time point may include at least one of the freshness of the common object at the second time point, the ripeness of the common object at the second time point, whether or not the common object is consumable at the second time point, or information about a consumable period of the common object at the second time point (for example, information about a remaining period until an expected disposal date), but it is not limited thereto.

In operation S1740, the refrigerator 1000 may adjust the image detection interval of the camera based on at least one of the information related to the state of the at least one object at the second time point or the degree of the change in the state of the at least one object.

According to an embodiment of the disclosure, the refrigerator 1000 may adjust the image detection interval of the camera based on the information related to the state of the common object at the second time point. For example, when a current state of the common object is a fresh state, the processor of the refrigerator 1000 may adjust the image detection interval to be great (for example, a day), and when the current state of the common object is a spoiled state, the processor of the refrigerator 1000 may adjust the image detection interval of the camera to be less (for example, thirty (30) minutes). Also, the processor of the refrigerator 1000 may adjust the image detection interval of the camera according to the period remaining until the expected disposal date. For example, as the time remaining until the expected disposal date gets shorter, the refrigerator 1000 may decrease the image detection interval of the camera.

According to an embodiment of the disclosure, the refrigerator 1000 may adjust the image detection interval of the camera based on the degree of the change in the state of the common object between the first time point and the second time point. For example, when the degree of the change in the state of the common object between the first time point and the second time point is great, the refrigerator 1000 may decrease the image detection interval of the camera (for example, from a day to six (6) hours). On the contrary, when the degree of the change in the state of the common object between the first time point and the second time point is less, the refrigerator 1000 may increase the image detection interval of the camera (for example, a day to three (3) days).

Hereinafter, an operation of adjusting the image detection interval of the camera by the refrigerator 1000 will be described in more detail with reference to FIGS. 18 and 19.

Figure 18:
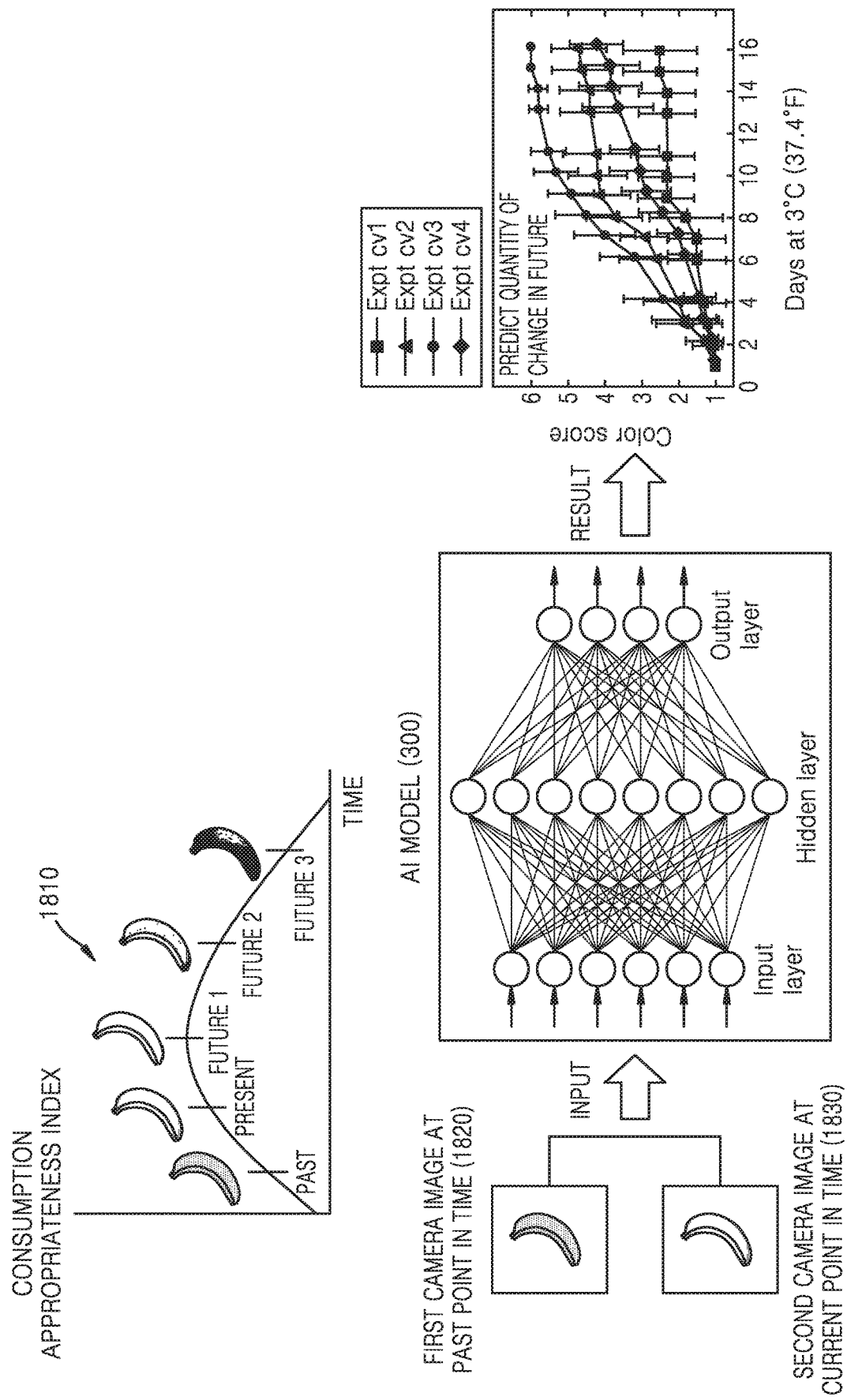
FIG. 18 is a flowchart of an operation of predicting a degree of change in a future state of an object, according to an embodiment of the disclosure.

FIG. 18 is a flowchart of an operation of predicting a quantity of a change in a future state of an object, according to an embodiment of the disclosure. In FIG. 18, an example in which the object is a banana will be described.

A consumption appropriateness index of the banana may vary according to a time. For example, with reference to a graph 1810, the consumption appropriateness index of the banana is the highest at a future time point 1 and the banana may not be ripe yet at a past time point and a current time point before the future time point 1. The banana may become ripe and start to get spoiled from a future time point 2 to a future time point 3 and the banana at the future time point 3 may be in a state in which the banana has to be disposed.

According to an embodiment of the disclosure, the refrigerator 1000 may store a first camera image 1820 at the past time point and when a second camera image 1830 at the current time point is obtained, may apply the first camera image 1820 and the second camera image 1830 to the AI model 300. Here, the AI model 300 may predict the change of the banana at the future time point based on the first camera image 1820 and the second camera image 1830.

Thus, according to an embodiment of the disclosure, the refrigerator 1000 may determine a time point to obtain a next camera image with respect to the banana after the current time point, based on a value generated by predicting the change of the banana in the future time point by the AI model 300. For example, when a quick change in the state of the banana is predicted, the refrigerator 1000 may determine the time point to obtain the next camera image as after two (2) hours, and when a slow change in the state of the banana is predicted, the refrigerator 1000 may determine the time point to obtain the next camera image as after one (1) day.

FIG. 19 is a view for describing an image detection interval of a camera, according to an embodiment of the disclosure.

According to an embodiment of the disclosure, the refrigerator 1000 may provide a first type of method 1910 in which a camera image is detected when a door of the refrigerator 1000 is opened and closed and a second type of method 1902 in which the image detection interval is adjusted according to a state of an object.

According to the first type of method 1910, there may be almost no problem, when a user frequently opens and closes the door of the refrigerator 1000. However, when the user rarely opens and closes the door of the refrigerator 1000, the user may miss the consumable period of the object. For example, the user may open and close the door of the refrigerator 1000 at time point 3, which is after seven (7) days after the user opened and closed the door of the refrigerator 1000 at a time point 1 and a time point 2 before a banana was ripe. In this case, the refrigerator 1000 may not be able to give notification about the edibility of the banana to the user within the consumable period of the banana.

However, according to the second type of method 1920, the refrigerator 1000 may adjust the image detection interval according to the state of the banana, and thus, the refrigerator 1000 may provide the notification with respect to the edibility of the banana to the user within the consumable period of the banana. For example, the refrigerator 1000 may adjust the image detection interval to be great before the banana is ripe (for example, before the time point 3) and may decrease the image detection interval after the banana is ripe. Thus, even when the user does not open and close the door of the refrigerator 1000 between the time point 3 and time point 6, the refrigerator 1000 may provide the notification that the banana is consumable to the user, to drive the user to consume the banana.

According to an embodiment of the disclosure, the refrigerator 1000 may select one of the first type of method 1910 and the second type of method 1920. For example, the refrigerator 1000 may obtain the camera image of a food item having a long consumable period by using the first type of method 1910 and may obtain the camera image of a food item having a short consumable period by using the second type of method 1920, but it is not limited thereto.

Figure 20:
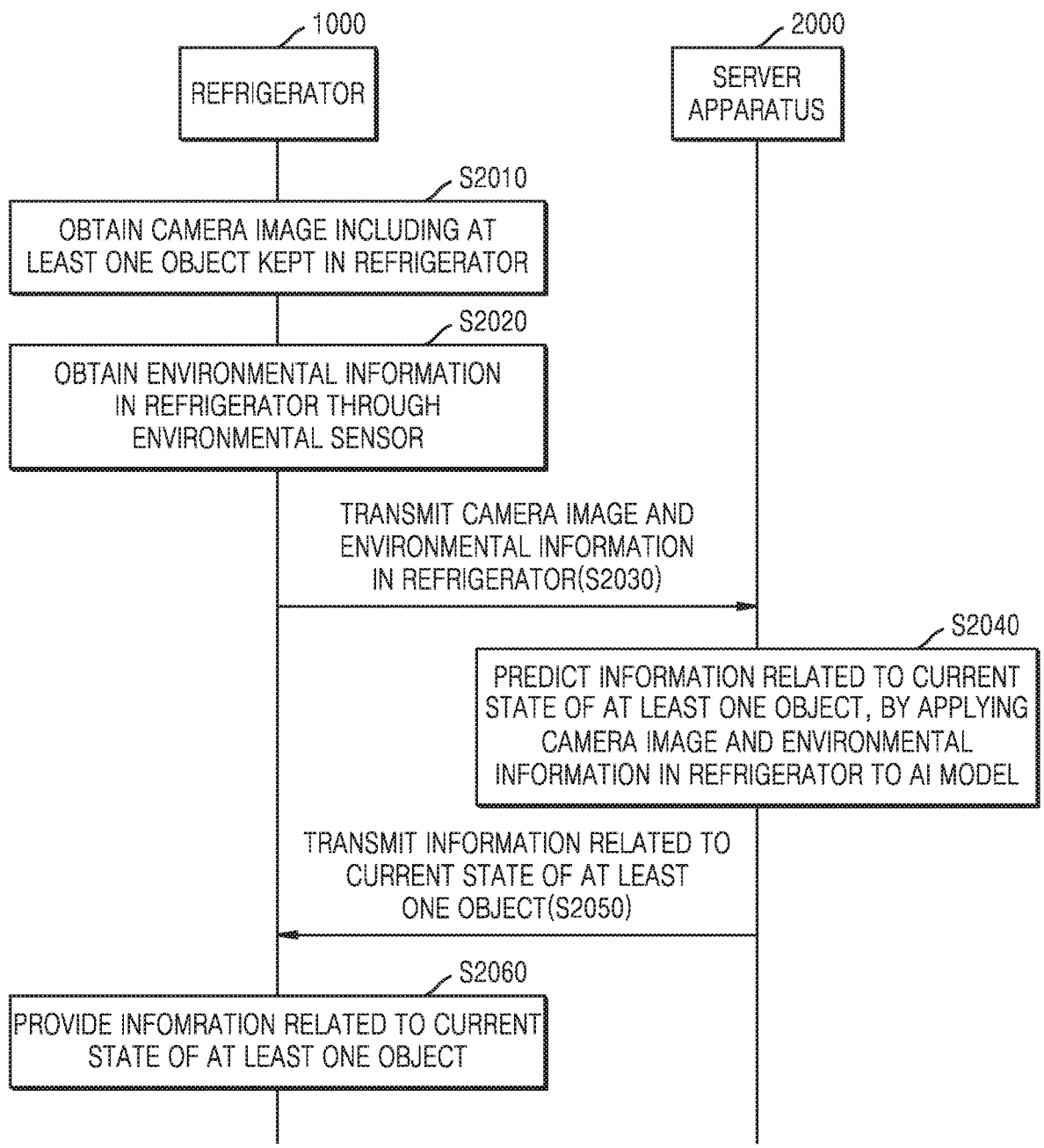
FIG. 20 is a flowchart of a method of providing information related to a state of at least one object, based on interconnection between a refrigerator and a server, according to an embodiment of the disclosure.

FIG. 20 is a flowchart of a method of providing information related to a state of at least one object based on interconnection between the refrigerator 1000 and the server apparatus 2000, according to an embodiment of the disclosure.

In operation S2010, the refrigerator 1000 may obtain a camera image including the at least one object kept in the refrigerator 1000.

According to an embodiment of the disclosure, the camera image may be an RGB image. The camera image may include one object or a plurality of objects. Operation S2010 corresponds to operation S210 of FIG. 2, and thus, its detailed description will be omitted.

In operation S2020, the refrigerator 1000 may obtain environmental information in the refrigerator 1000 through an environmental sensor arranged in the refrigerator 1000.

According to an embodiment of the disclosure, the environmental sensor may include at least one of a temperature sensor, a humidity sensor, or an odor sensor, but it is not limited thereto. According to an embodiment of the disclosure, the environmental information in the refrigerator 1000 may be information about an environment in the refrigerator 1000, and may include, for example, at least one of temperature information, humidity information, or odor information. Operation S2020 corresponds to operation S220 of FIG. 2, and thus, its detailed description will be omitted.

In operation S2030, the refrigerator 1000 may transmit the camera image and the environmental information in the refrigerator 1000 to the server apparatus 2000.

Here, according to an embodiment of the disclosure, the refrigerator 1000 may request information related to a current state of the at least one object included in the camera by transmitting identification information of the refrigerator 1000 or identification information (for example, account information) of a user to the server apparatus 2000.

In operation S2040, the server apparatus 2000 may predict the information related to the current state of the at least one object by applying the camera image and the environmental information in the refrigerator 1000 to the AI model 300.

According to an embodiment of the disclosure, the server apparatus 2000 may predict a current state of at least one object, a consumable period (or an expected disposal point) based on the current state, information about a change in a state after a predetermined time from a current point in time, etc., but it is not limited thereto.

According to an embodiment of the disclosure, the server apparatus 2000 may predict the current state of the at least one object by applying the camera image including the at least one object and the temperature information (or the humidity information) around the at least one object to the AI model 300. Here, the AI model 300 may be an artificial neural network trained using the camera image, the temperature information (or the humidity information), and the state of the object as learning data.

According to an embodiment of the disclosure, the server apparatus 2000 may predict the current state of the at least one object by applying the camera image including the at least one object and the odor information of the at least one object to the AI model 300. According to an embodiment of the disclosure, the server apparatus 2000 may predict the current state of the at least one object by applying the camera image including the at least one object, the temperature information (or the humidity information) around the at least one object, and the odor information of the at least one object to the AI model 300. Also, the server apparatus 2000 may predict the current state of the at least one object by applying the camera image including the at least one object, the temperature information around the at least one object, the humidity information around the at least one object, and the odor information of the at least one object to the AI model 300.

According to an embodiment of the disclosure, when the current state of the at least one object is not a spoiled state, the AI model 300 may predict the consumable period (for example, the remaining period from a current point in time to an expected disposal date) of the at least one object. For example, the AI model 300 may determine that the current state of a banana is a ripe state and the remaining period until the expected disposal date is three (3) days, based on the camera image including the banana and the environmental information around the banana. In this case, the AI model 300 may transmit the information about the current state (for example, the ripe state) of the banana and the remaining period (for example, three (3) days) until the expected disposal date to a processor of the server apparatus 2000.

Meanwhile, according to an embodiment of the disclosure, the server apparatus 2000 may further accurately predict the current state of the at least one object by further applying a spectrometric image to the AI model 300 in addition to the camera image and the environmental information. The operation of using the spectrometric image by the AI model 300 is described with reference to FIG. 6, and thus, its detailed description will be omitted.

In operation S2050, the server apparatus 2000 may transmit the information related to the current state of the at least one object to the refrigerator 1000.

According to an embodiment of the disclosure, the server apparatus 2000 may transmit the information related to the current state of the at least one object to the refrigerator 1000 based on the identification information of the refrigerator 1000 or the identification information of the user received from the refrigerator 1000. For example, the server apparatus 2000 may transmit at least one of the freshness of the at last one object, the ripeness of the at least one object, the edibility of the at least one object, or information about the consumable period of the at least one object (for example, information about the remaining period until the expected disposal date) to the refrigerator 1000.

Meanwhile, according to an embodiment of the disclosure, when the mobile terminal 3000 of the user is registered in the server apparatus 2000, the server apparatus 200 may provide the information (for example, the freshness, the ripeness, the edibility, the consumable period, etc.) related to the current state of the at least one object kept in the refrigerator 1000 to the mobile terminal 3000 of the user.

In operation S2060, the refrigerator 1000 may output the information related to the current state of the at least one object.

According to an embodiment of the disclosure, the refrigerator 1000 may provide the information about the consumable period of the at least one object, based on the current state of the at least one object. According to an embodiment of the disclosure, the refrigerator 1000 may display the information about the consumable period on the camera image including the at least one object in an overlapping manner. Meanwhile, according to an embodiment of the disclosure, the refrigerator 1000 may display the expected disposal date in different colors according to the extent of the consumable period.

According to an embodiment of the disclosure, the refrigerator 1000 may display the information about the consumable period of the objects kept in the refrigerator 1000 in the form of a list. For example, the refrigerator 1000 may provide the list of the objects by displaying the list such that an object having a less consumable period is displayed above.

According to an embodiment of the disclosure, the refrigerator 1000 may provide the information about the ripeness or the freshness of the at least one object. According to an embodiment of the disclosure, the refrigerator 1000 may provide the information related to the current state of the at least one object through the display of the refrigerator 1000 or the mobile terminal 3000.

Operation S2060 corresponds to operation S240 of FIG. 2, and thus, its detailed description will be omitted.

Figure 21:
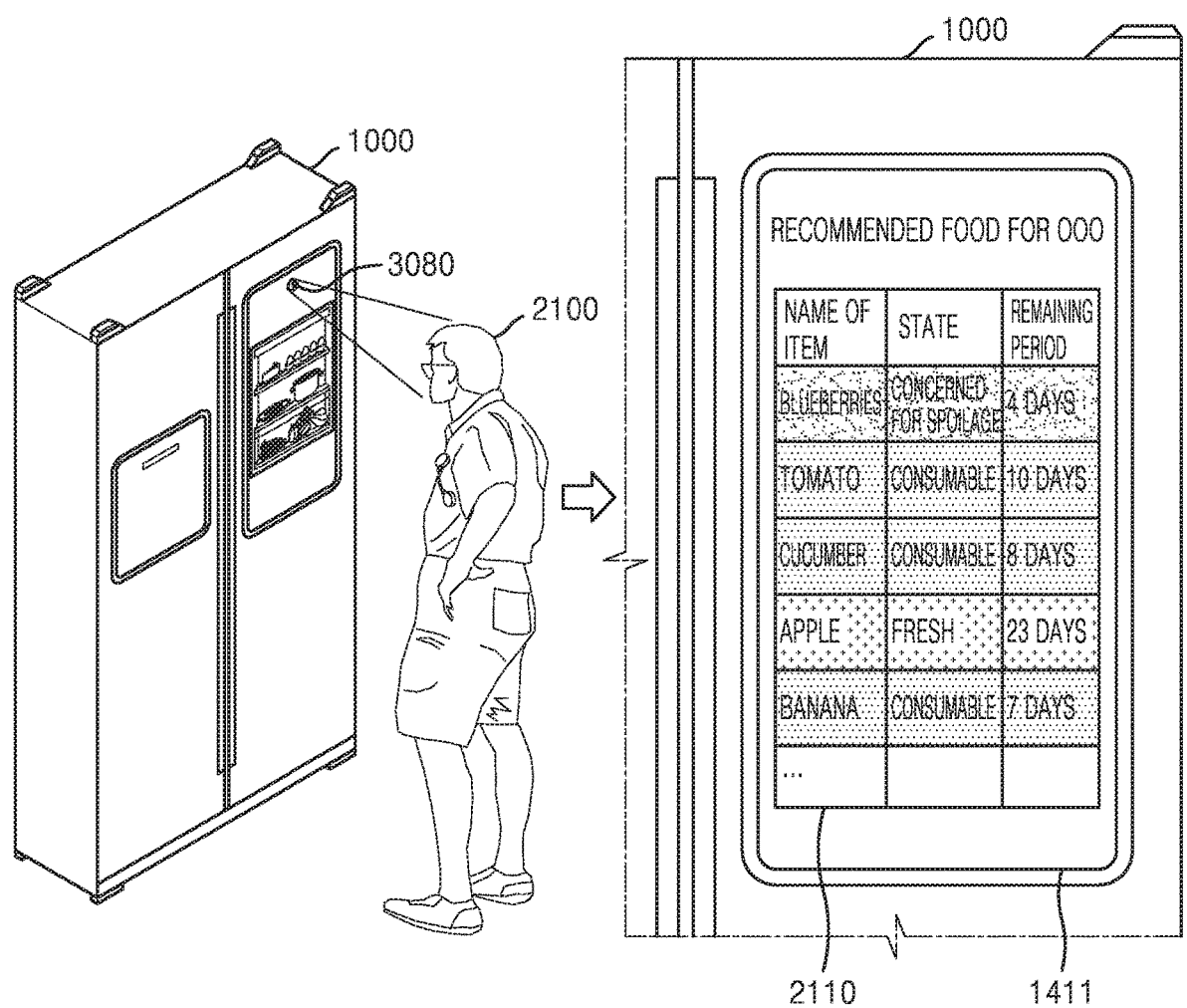
FIG. 21 is a view for describing an operation, performed by a processor of a refrigerator, of recommending a food item in a refrigerator for each user, according to an embodiment of the disclosure.

FIG. 21 is a view for describing an operation, performed by a processor of the refrigerator 1000, of recommending a food item in the refrigerator 1000 for each user, according to an embodiment of the disclosure.

Referring to FIG. 21, the refrigerator 1000 may identify a user 2100 approaching the refrigerator 1000 via a camera 3080 arranged outside the refrigerator 1000. Also, the refrigerator 1000 may identify the user 2100 based on a voice of the user 2010 recognized via a microphone.

When the refrigerator 1000 identifies the user 2100, the refrigerator 1000 may recommend a food item for the user 2100 that is identified, from among the food items kept in the refrigerator 1000. According to an embodiment of the disclosure, the refrigerator 1000 may recommend the food item to the user 2100 by taking into account at least one of information about user's preferred food, a health state of the user 2100, current time, or a consumable period of the food item. For example, when the current time is three (3) μm, and the user 2100 prefers to have fruit for snacks at three (3) μm and the user 2100 has diabetes, the refrigerator 1000 may recommend to the user 2100 fruits which are within the consumable period, based on the order in which consumption of the corresponding fruit does not overly raise a blood sugar level. For example, the refrigerator 1000 may provide a recommend food list 2110 including blueberries, a tomato, a cucumber, an apple, and a banana to the user 2100. Here, the recommend food list 2110 may include names of the food, states of the food, and remaining times until expected disposal dates.

When the user 2100 selects one from the recommend food list 2110, the refrigerator 1000 may display a location in which the selected food is kept, on a camera image in the refrigerator 1000. For example, when the user 2100 selects (for example, touches) blueberries from the recommend food list 2110, the refrigerator 1000 may provide the information that the blueberries are kept in a first shelf on a right bottom portion to the user 2100. For example, the refrigerator 1000 may display an identification mark on the blueberries on the camera image in the refrigerator 1000.

FIG. 21 illustrates the example in which the camera 3080 is arranged above the display 1411. However, it is not limited thereto. For example, the camera 3080 may be located below the display 1411 or may be arranged at a right door.

Figure 22:
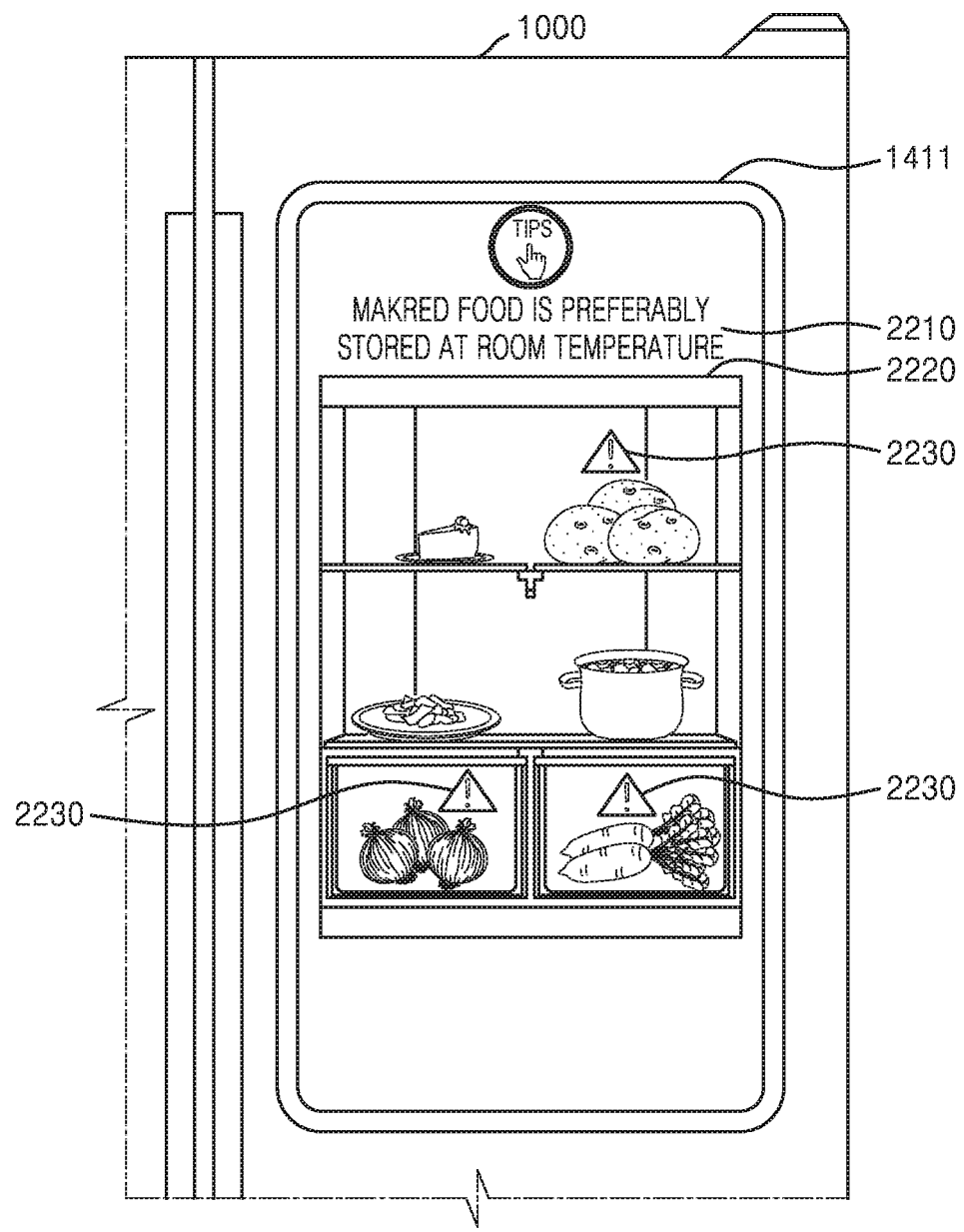
FIG. 22 is a view for describing an operation, performed by a refrigerator, of providing guide information about food items to be kept at room temperature, according to an embodiment of the disclosure.

FIG. 22 is a view for describing an operation, performed by the refrigerator 1000, of providing guide information about food items to be stored at room temperature, according to an embodiment of the disclosure.

According to an embodiment of the disclosure, the refrigerator 1000 may identify at least one object based on a result of analyzing a camera image. For example, a processor of the refrigerator 1000 may detect a type of the at least one object, a name of the at least one object, etc., by comparing an outline of the at least one object included in the camera image with a pre-defined template. According to an embodiment of the disclosure, the refrigerator 1000 may identify the at least one object included in the camera image by applying the camera image to the AI model 300.

For example, the refrigerator 1000 may identify a cake, a potato, an onion, a radish, etc. on the camera image 2220 including the objects kept in the refrigerator 1000.

According to an embodiment of the disclosure, the refrigerator 1000 may select an object to be kept at room temperature from among the objects identified on the camera image, based on food storage guideline information. For example, the refrigerator 1000 may identify the potato, the onion, and the radish as the objects to be stored at room temperature.

According to an embodiment of the disclosure, the refrigerator 1000 may display an attention mark 2230 on each of the potato, the onion, and the radish included in the camera image 2220. Also, the refrigerator 1000 may provide guide information 2210 (for example, the marked item is preferably stored at room temperature) about a storage method, together with the camera image 2220.

According to an embodiment of the disclosure, when a user selects one of the attention marks displayed on the objects, the refrigerator 1000 may provide detailed information about the storage method of the corresponding object. For example, when the user selects (for example, touches) the mark on the potato, the detailed information about the storage method of the potato (for example, a potato is a vegetable containing much water, and thus, when the potato is refrigerated, the potato may absorb the odor of other foods stored together. Thus, it is required to store the potato at room temperature by wrapping the potato by using a paper, such a newspaper. A plastic material captures the water to facilitate the speed of spoilage, so avoid the plastic material!).

Figure 23:
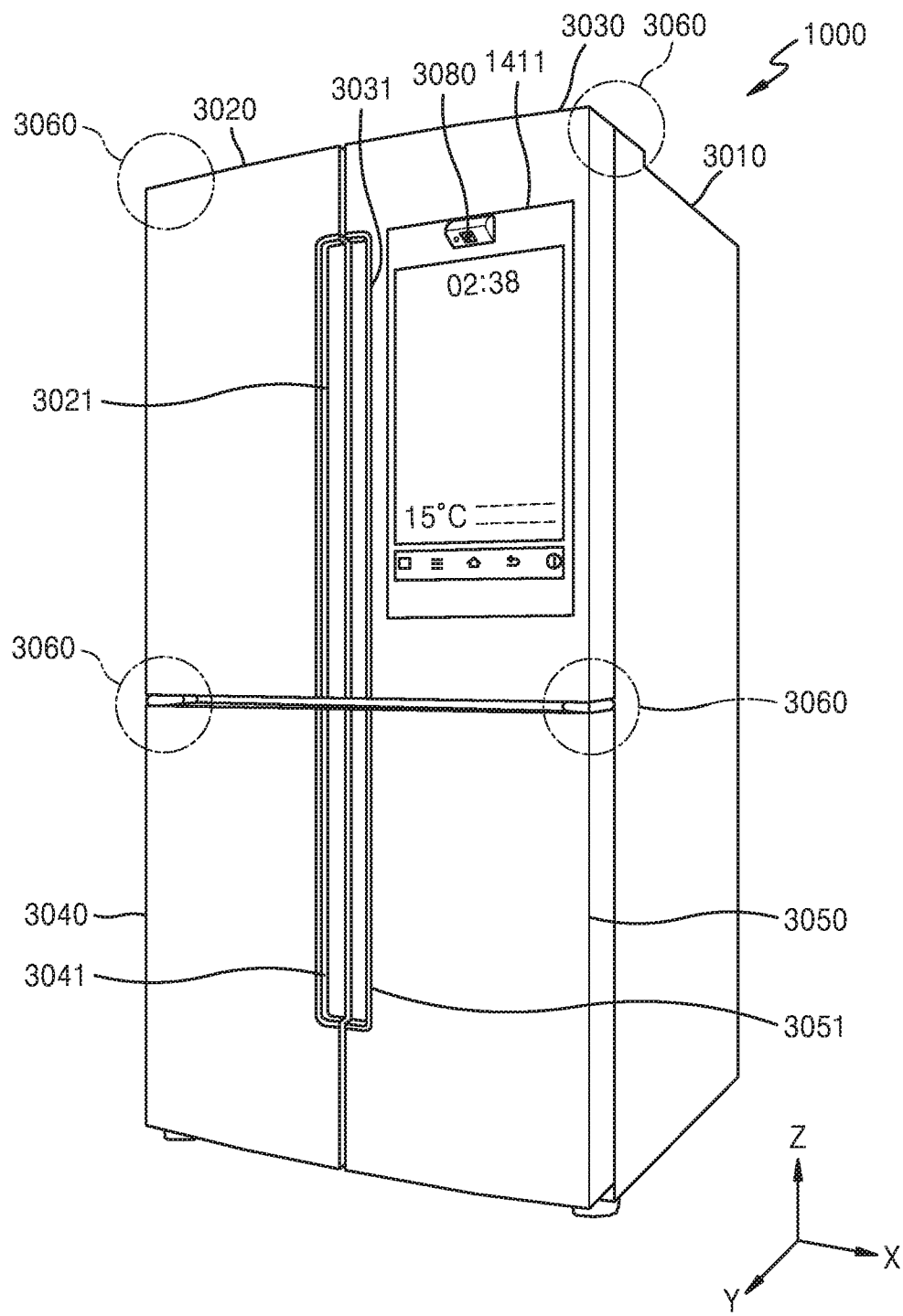
FIGS. 23 and 24 are views for describing a structure of a refrigerator according to an embodiment of the disclosure.
Figure 24:
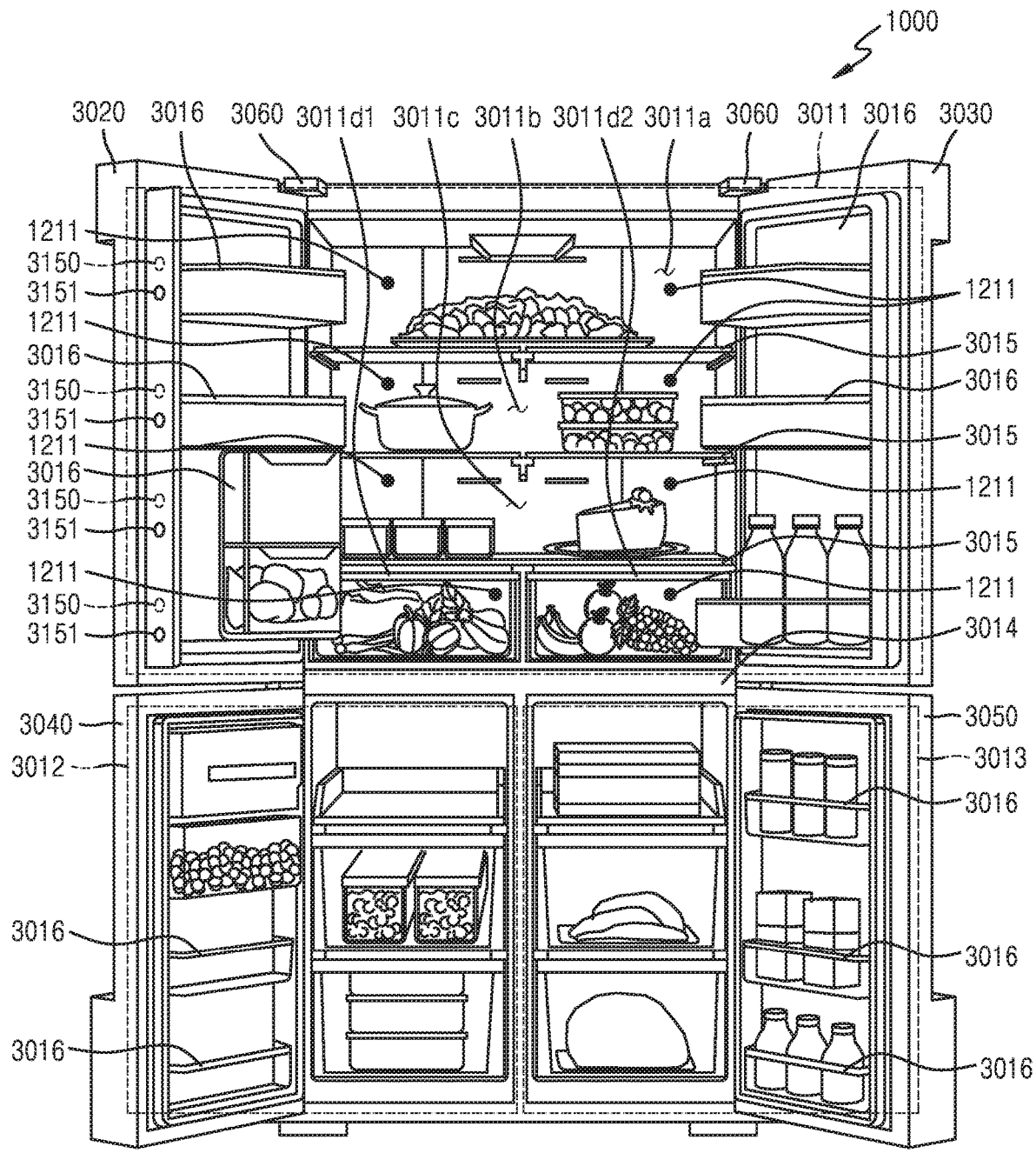

FIGS. 23 and 24 are views for describing a structure of the refrigerator 1000, according to an embodiment of the disclosure.

Referring to FIGS. 23 and 24, the refrigerator 1000 may include a main body 3010, storerooms 3011, 3012, and 3013, a plurality of doors 3020, 3030, 3040, and 3050, and a hinge 3060 connecting each of the doors 3020, 3030, 3040, and 3050 to the main body 3010. The display 1411 displaying content may be located on at least one door (for example, at least one of the door 3030 on the right side or the door 3020 on the left side) from among the plurality of doors 3020, 3030, 3040, and 3050.

A camera (or a front camera 3080) may be located in at least one door (for example, at least one of the door 3030 on the right side or the door 3020 on the left side) from among the plurality of doors 3020, 3030, 3040, and 3050. A proximity sensor portion (not shown) may be located to be adjacent (for example, within a radius of 500 mm) to the front camera 3080. Also, a microphone (not shown) may be located in at least one door (for example, at least one of the door 3030 on the right side or the door 3020 on the left side) from among the plurality of doors 3020, 3030, 3040, and 3050.

Types of the refrigerator 1000 may be divided according to the forms of the storerooms and the doors. In the case of a top mounted freezer (TMP) type refrigerator, a freezing room may be formed above and a refrigerating room may be formed below. However, in the case of a bottom mounted freezer (BMF) type refrigerator, a refrigerating room may be formed above and a freezing room may be formed below. A side by side (SBS) type refrigerator may have a freezing room on the left side (or the right side) and a refrigerating room on the right side (or on the left side). A French door refrigerator (FDR) type refrigerator may be divided into an upper portion and a lower portion by a partition, and a refrigerating room may be formed in the upper portion and a freezing room may be formed in the lower portion, where the refrigerating room in the upper portion may be opened and closed by a pair of doors. Also, in the case of the FDR type refrigerator, both of the refrigerating room in the upper portion and the freezing room in the lower portion may be opened and closed by a pair of doors.

The main body 3010 may include an inner case (not shown) forming the storerooms 3011 through 3013, an outer case (not shown) forming an exterior of the refrigerator 1000, and an insulator (not shown) keeping a temperature difference between the inner case and the outer case. The insulator may prevent cold air in the storerooms 3011 through 3013 from being discharged to the outside and hot air from the outside of the storerooms 3011 through 3013 from being introduced into the storerooms 3011 through 3013.

The main body may include a cold air supply unit configured to supply cold air to the storerooms 3011 through 3013. The cold air supply unit may include a compressor (not shown) to compress a refrigerant, a condenser (not shown), an expansion valve (not shown), an evaporator (not shown), and a pipe.

The storerooms 3011 through 3013 may be divided by a partition 3014. The storerooms 3011 through 3013 may be divided into freezing storerooms 3012 and 3013 (hereinafter, referred to as "freezing rooms") below and a cooling storeroom 3011 (hereinafter, referred to as a "refrigerating room") above the freezing storerooms 3012 and 3013. The storerooms 3011 through 3013 may be set to have temperatures above zero (for example, between 7° C. and 0° C.) or below zero (for example, between −1° C. and −5° C.) and may accommodate water, beverages, food stuffs, chilled foods, or frozen foods. Water or beverages may be accommodated in a beverage container.

The refrigerating room 3011 among the storerooms 3011 through 3013 divided by the partition 3014 may include one or more shelves 3015 and one or more storage boxes 3016.

The refrigerating room 3011 may be adjacent to the first door 3020 at a side (for example, the left side) of the storeroom 3011 and may be coupled to the second door 3030 that is adjacent to the first door 3020 and located at the other side (for example, the right side) of the storeroom 3011. The first door 3020 and/or the second door 3030 may rotate at an angle (for example, an angle equal to or less than 300°) set by the hinge 3060 corresponding to each of the first door 3020 and the second door 3030, to open and close (for example, to be coupled to or separated from) a front surface of the storeroom 3011. The first door 3020 may rotate in a direction opposite to a direction in which the second door 3030 rotates, to open and close the storeroom 3011. Locations of the first door 3020 and the second door 3030 may be changed with each other.

The first door 3020 may rotate at the angle (for example, the angle equal to or less than 300°) set by the hinge 3060 to open and close a portion (for example, between 35% and 70% of the front surface of the storeroom 3011) of the front surface of the storeroom 3011.

A dispenser providing water, ice, or sparkling water and/or a handle 3021 which may be grasped may be located at the front surface (for example, a +y axis directions) of the first door 3020.

The second door 3030 may rotate at the angle (for example, the angle equal to or less than 300°) set by the hinge 3060 to open and close a portion (for example, between 35% and 70% of the front surface of the storeroom 3011) of the front surface of the storeroom 3011. The second door 3030 may include a handle 3031 which may be grasped. The handle 3021 of the first door 3020 and the handle 3031 of the second door 3030 may be located at the left side and the right side to be apart from each other based on the central area of the storeroom 3011.

The display (or a touch screen) 1411 may be located at the front surface (for example, a +y axis direction) of the second door 3030. The display 1411 may display functions and stored settings of the refrigerator 1000. The display 1411 may receive a user's input (for example, a touching operation or an operation of selecting a button (not shown)). Here, the button may be included in the display 1411 or may be separate from the display 1411. The button may include a software button and a hardware button. The display 1411 may display (or execute) a screen of an application (including a widget).

Vegetable boxes 3011*d*1 and 3011*d*2 may be located below the storeroom 3011. The vegetable boxes 3011*d*1 and 3011*d*2 may be withdrawn (for example, slided or rolled) forward (for example, a y axis direction).

The storerooms 3012 and 3013 may have the doors 3040 and 3050 at sides thereof. The storerooms 3012 and 3013 may be integrated into one storeroom (for example, like the storeroom 3011). Also, the refrigerator 1000 may have a drawer.

Meanwhile, the refrigerator 1000 may include an inner camera 3150 to capture the inside space of the refrigerator 1000, a spectrometric camera 3151 to obtain a spectrometric image in the refrigerator 1000, and an environmental sensor 1211 (for example, an odor sensor, a temperature sensor, or a humidity sensor).

Figure 25:
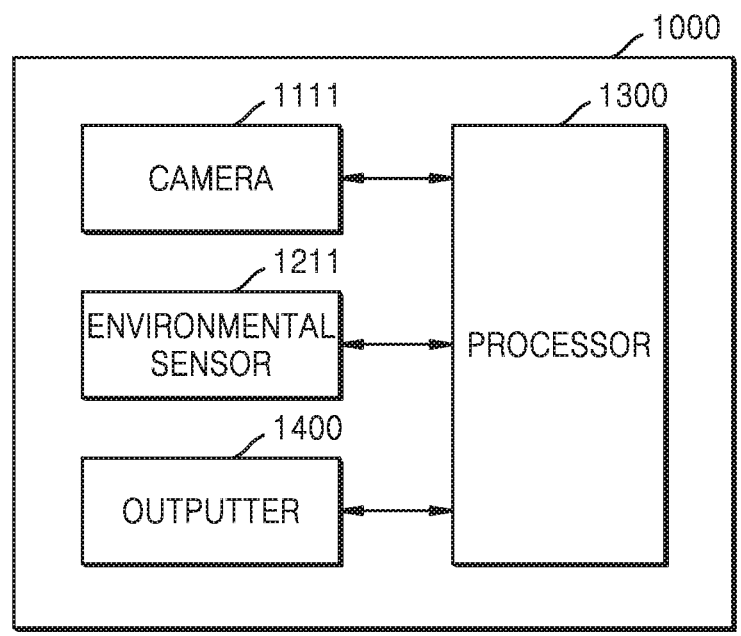
FIGS. 25 and 26 are block diagrams for describing a function of a refrigerator according to an embodiment of the disclosure.
Figure 26:
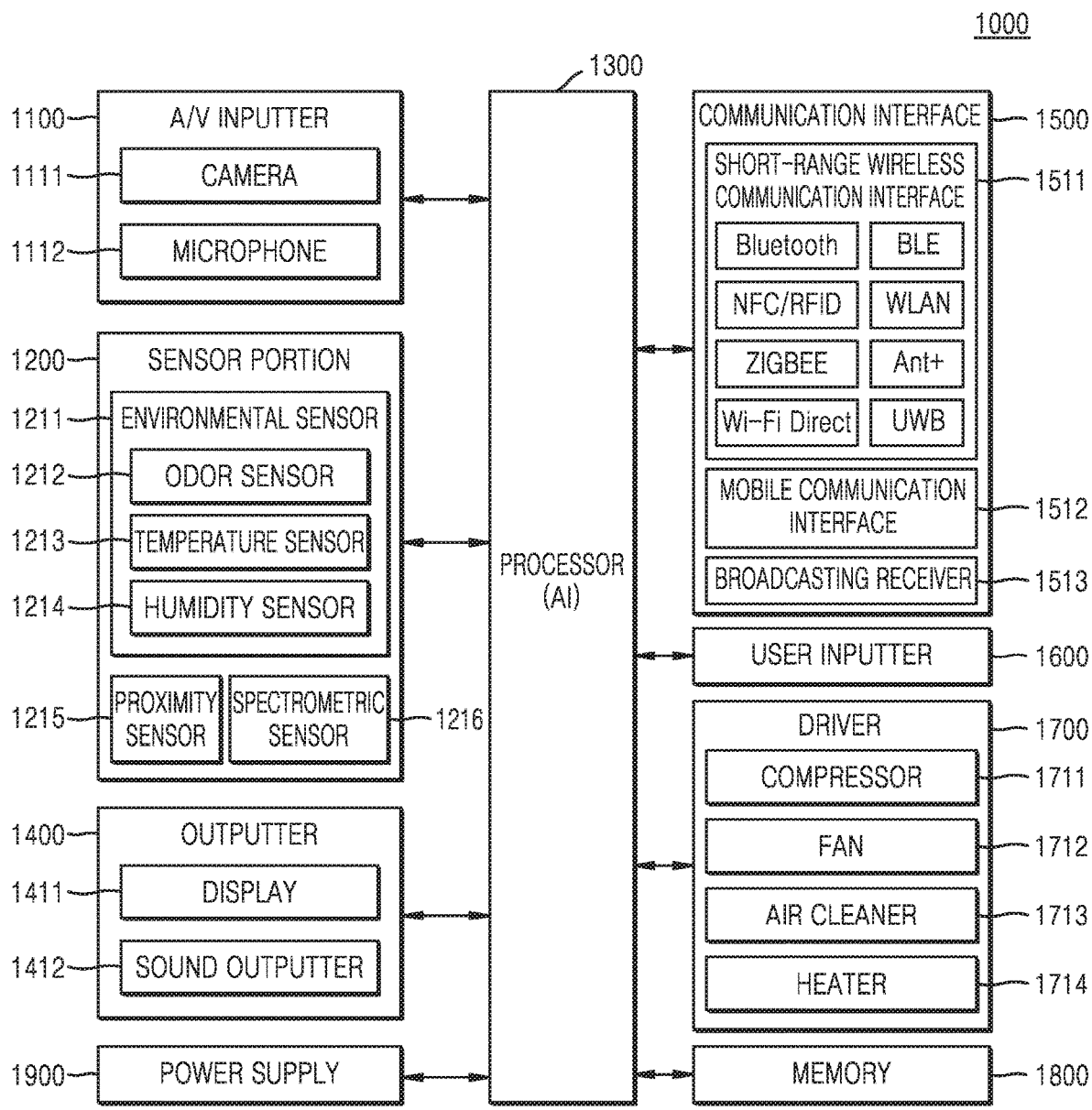

FIGS. 25 and 26 are block diagrams for describing functions of the refrigerator 1000 according to an embodiment of the disclosure.

As illustrated in FIG. 25, the refrigerator 1000 according to an embodiment of the disclosure may include a camera 1111, the environmental sensor 1211, a processor 1300, and an outputter 1400. However, not all illustrated components are essential components. The refrigerator 1000 may be realized by including more or less components than the illustrated components. For example, as illustrated in FIG. 26, the refrigerator 1000 according to an embodiment of the disclosure may include an audio/video (A/V) inputter 1100, a sensor portion 1200, the processor 1300, the outputter 1400, a communication interface 1500, a user inputter 1600, a driver 1700, a memory 1800, and a power supply 1900.

Hereinafter, the components above will be sequentially described.

The A/V inputter 1100 may be included for an input of an audio signal or a video signal and may include the camera 1111, a microphone 1112, etc. The camera 1111 may obtain an image frame, such as a still image or a video, via an image sensor. The image captured by the image sensor may be processed by the processor 1300 or an additional image processing interface (not shown).

According to an embodiment of the disclosure, the camera 1111 may include an outer camera to capture an outer environment and an inner camera 3150 to capture an inner environment. The inner camera 3150 to capture the inner environment may be provided in a multiple number. The camera 1111 may obtain a camera image (for example, RGB) including at least one object kept in the refrigerator 1000 via the inner camera 3150.

The microphone 1112 may receive an external sound signal and process the external sound signal into electrical sound data. For example, the microphone 1112 may receive a sound signal (for example, a voice command) from an external device or a speaker. The microphone 1112 may use various noise removal algorithms to remove noise occurring in the process of receiving the external sound signal.

The sensor portion 1200 may include at least one of the environmental sensor 1211, a proximity sensor 1215, or a spectrometric sensor 1216, but it is not limited thereto. The environmental sensor 1211 may be a sensor to obtain the environmental information in the refrigerator 1000 and may include at least one of one or more odor sensors 1212, a temperature sensor 1213, or a humidity sensor 1214. The spectrometric sensor 1216 may be a spectrometric camera 3151 of FIG. 24. The function of each of the sensors may be intuitively inferred by one of ordinary skill in the art from its name, and thus, its detailed description will be omitted.

The processor 1300 may generally control general operations of the refrigerator 1000. For example, the processor 1300 may execute programs stored in the memory 1800 to generally control the A/V inputter 1100, the sensor portion 1200, the outputter 1400, the communication interface 1500, the user inputter 1600, the driver 1700, the memory 1800, the power supply 1900, etc.

According to an embodiment of the disclosure, the processor 1300 may include an AI processor configured to generate a learning network model, but it is not limited thereto. According to an embodiment of the disclosure, the AI processor may be realized as a chip separate from the processor 1300. According to an embodiment of the disclosure, the AI processor may be a general-purpose chip.

According to an embodiment of the disclosure, the processor 1300 may predict a current state of at least one object kept in the refrigerator 1000, by applying a camera image including the at least one object and environmental information in the refrigerator 1000 to the AI model 300.

For example, the processor 1300 may obtain temperature information around the at least one object by using the temperature sensor 1213 and apply the camera image including the at least one object and the temperature information around the at least one object to the AI model 300 to predict the current state of the at least one object.

The processor 1300 may obtain odor information of the at least one object by the odor sensor 1212 arranged to be adjacent to the at least one object and apply the camera image including the at least one object and the odor information of the at least one object to the AI model 300 to predict the current state of the at least one object.

The processor 1300 may obtain a spectrometric image about the at least one object by using the spectrometric sensor 1216 arranged in the refrigerator 1000. The processor 1300 may apply the camera image including the at least one object, the spectrometric image, and the environmental information in the refrigerator 1000 to the AI model 300 to predict the current state of the at least one object.

The processor 1300 may determine whether a gas detection quantity measured by at least one odor sensor from among the plurality of odor sensors 1212 arranged in the refrigerator 1000 is greater than a critical value. When the gas detection quantity is greater than the critical value, the processor 1300 may generate an odor distribution map based on the odor information obtained from the plurality of odor sensors 1212. The processor 1300 may compare the camera image including the at least one object and the odor distribution map to identify a first object having a spoilage probability greater than a reference value.

The processor 1300 may obtain spectrometric information about the first object by using the spectrometric sensor 1216 arranged in the refrigerator 1000. The processor 1300 may determine a degree of spoilage of the first object by using the spectrometric information.

The outputter 1400 may be included to output an audio signal, a video signal, or a vibration signal and may include the display 1411, the sound outputter 1412, a vibration motor (not shown), etc.

When the display 1411 and a touch pad are layered to form a touch screen, the display 1411 may be used as an input device as well as the output device. The display 1411 may include at least one of a liquid crystal display, a thin film transistor-liquid crystal display, an organic light-emitting diode, a flexible display, a 3D display, or an electrophoretic display. Also, according to a form in which the refrigerator 1000 is realized, the refrigerator 1000 may include two or more displays 1411.

The sound outputter 1412 may output audio data received from the communication interface 1500 or stored in the memory 1800. Also, the sound outputter 1412 may output sound signals related to functions (for example, a call signal reception sound, a message reception sound, a notification sound, etc.) performed by the refrigerator 1000. The sound outputter 1412 may include a speaker, a buzzer, etc.

The outputter 1400 may provide the information related to the current state of the at least one object. The outputter 1400 may visually provide the information related to the current state of the least one object via the display 1411 and may acoustically provide the information related to the current state of the least one object via the sound outputter 1412. Here, the information related to the current state of the at least one object may include at least one of information about a consumable period of the at least one object, information about the ripeness of the at least one object, or information about the freshness of the at least one object, but it is not limited thereto.

The communication interface 1500 may include one or more components to enable communication between the refrigerator 1000 and the server apparatus 2000 and between the refrigerator 1000 and the mobile terminal 3000. For example, the communication interface 1500 may include a short-range wireless communication interface 1511, a mobile communication interface 1512, and a broadcasting receiver 1513.

The short-range wireless communication interface 1511 may include a Bluetooth communication interface, a BLE communication interface, a near-field communication interface, a WLAN (Wi-Fi) communication interface, a Zigbee communication interface, an IrDA communication interface, a WFD (Wi-Fi direct) communication interface, a UWB communication interface, an ANT+ communication interface, etc., but it is not limited thereto.

The mobile communication interface 1512 may transmit and receive wireless signals to and from at least one of a base station, an external terminal, or a server, in a mobile communication network. Here, the wireless signals may include a voice call signal, a video telephony call signal, or various types of data according to exchange of text/multimedia messages.

The broadcasting receiver 1513 may receive broadcasting signals and/or information related to broadcasting from the outside via broadcasting channels. The broadcasting channels may include a satellite channel and a ground wave channel. According to an embodiment of the disclosure, the refrigerator 1000 may not include the broadcasting receiver 1513.

The user inputter 1600 denotes a device for a user to input data for controlling the refrigerator 1000. For example, the user inputter 1600 may include a key pad, a dome switch, a touch pad (a touch capacitance method, a pressure resistive method, an infrared detection method, a surface ultrasonic conductive method, an integral tension measuring method, a piezo effect method, etc.), a jog wheel, a jog switch, etc., but it is not limited thereto.

The driver 1700 may include at least one of a compressor 1711, a fan 1712, an air cleaner 1713, or a heater 1714, which operates under control of the processor 1300. The driver 1700 may further include illuminator (or a deodorizer).

The compressor 1711 may compress a refrigerant which is a working fluid of a freezing cycle under control of the processor 1300. The freezing cycle may include a condenser to convert the refrigerant in a state of gas compressed by the compressor 1711 into the refrigerant in a state of liquid, an inflator to decompress the refrigerant in the state of liquid, and an evaporator to vaporize the decompressed refrigerant in the state of liquid. The processor 1300 may control temperatures of the storerooms through the vaporization of the refrigerant in the state of liquid. Also, the refrigerator 1000 may control the temperatures of the storerooms by using a Peltier device using the Peltier effect and a magnetic cooling device using the magnetocaloric effect.

The fan 1712 may circulate external air under control of the processor 1300. The air heated by the refrigerating cycle may be thermally exchanged through the external air to be cooled.

The air cleaner 1713 may sterilize (or remove) germs floating in or attached to the storerooms under control of the processor 1300. The air cleaner 1713 may include an ion sterilizer.

The heater 1714 may remove generated frost under control of the processor 1300. The heater 1714 may include a defrosting heater.

The memory 1800 may store programs for processing and controlling operations of the processor 1300 and store input/output data (for example, the camera image, the spectrometric image, the environmental information, the learning data, the recommend food list, the health information of the user, the information about the preference of the user, etc.).

The memory 1800 may include a memory of a flash memory type, a hard disk type, a multimedia card micro type, or a card type (for example, an SD or XD memory) and at least one type of storage medium from among random-access memory (RAM), static RAM (SRAM), read-only memory (ROM), electrically erasable programmable ROM (EEPROM), programmable ROM (PROM), magnetic memory, magnetic disks, or optical disks. The programs stored in the memory 1800 may be divided into a plurality of modules according to their functions.

The power supply 1900 may supply power to the components of the refrigerator 1000 under control of the processor 1300. The power supply 1900 may supply power input from an external power source via a power code to each of the components of the refrigerator 1000 under control of the processor 1300.

Hereinafter, a process in which the AI model 300 is generated will be described with reference to FIGS. 27 through 30. In FIGS. 27 through 30, the AI model 300 may be referred to as a recognition model.

Figure 27:
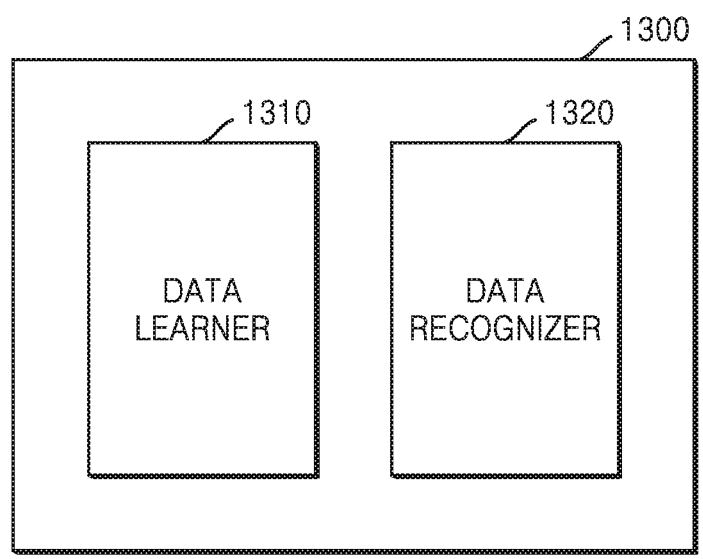
FIG. 27 is a block diagram of a processor according to an embodiment of the disclosure.

FIG. 27 is a block diagram of the processor 1300 according to an embodiment of the disclosure.

Referring to FIG. 27, the processor 1300 according to one or more embodiments of the disclosure may include a data learner 1310 and a data recognizer 1320.

The data learner 1310 may learn the reference for determining a state of an object (for example, the edibility, the consumable period, the expected disposal date, the freshness, the ripeness, the degree of spoilage, etc.). The data learner 1310 may learn the reference with respect to which data to use to determine the state of the object and how to determine the state of the object by using the data. The data learner 1310 may learn the reference for determining the state of the object by obtaining the data (for example, the camera image, the spectrometric image, and the environmental information) to be used for learning and applying the obtained data to a data recognition model to be described below.

The data recognizer 1320 may determine the state of the object based on the data. The data recognizer 1320 may recognize the state of the object from detected data, by using the trained data recognition model. The data recognizer 1320 may obtain image data (for example, obtain the camera image) according to a reference predetermined based on learning and use the data recognition model by using the obtained image data as an input value, to determine the state of the object based on the image data. Also, a result value output by the data recognition model by using the obtained image data as the input value may be used to refine the data recognition model.

At least one of the data learner 1310 or the data recognizer 1320 may be formed in the form of at least one hardware chip and mounted in the refrigerator 1000. For example, at least one of the data learner 1310 or the data recognizer 1320 may be formed in the form of an exclusive hardware chip for AI or may be formed as part of a general-purpose processor (for example, a central processing unit (CPU) or an application processor) or a graphics exclusive processor (for example, a graphics processing unit (GPU)) and mounted in the refrigerator 1000.

In this case, the data learner 1310 and the data recognizer 1320 may be mounted in one refrigerator 1000 or each may be mounted in a different electronic apparatus. For example, one of the data learner 1310 and the data recognizer 1320 may be included in the refrigerator 1000 and the other may be included in the server apparatus 2000. Also, the data learner 1310 and the data recognizer 1320 may communicate with each other in a wired or wireless manner to provide model information established by the data learner 1310 to the data recognizer 1320 or provide data input into the data recognizer 1320 to the data learner 1310 as additional learning data.

Meanwhile, at least one of the data learner 1310 or the data recognizer 1320 may be realized as a software module. When the at least one of the data learner 1310 or the data recognizer 1320 is realized as the software module (or a program module including an instruction), the software module may be stored in a non-transitory computer readable recording medium. Also, in this case, the at least one software module may be provided by an operating system (OS) or a certain application. Alternatively, a portion of the at least one software module may be provided by the OS and the other portion of the at least one software module may be provided by a certain application.

Figure 28:
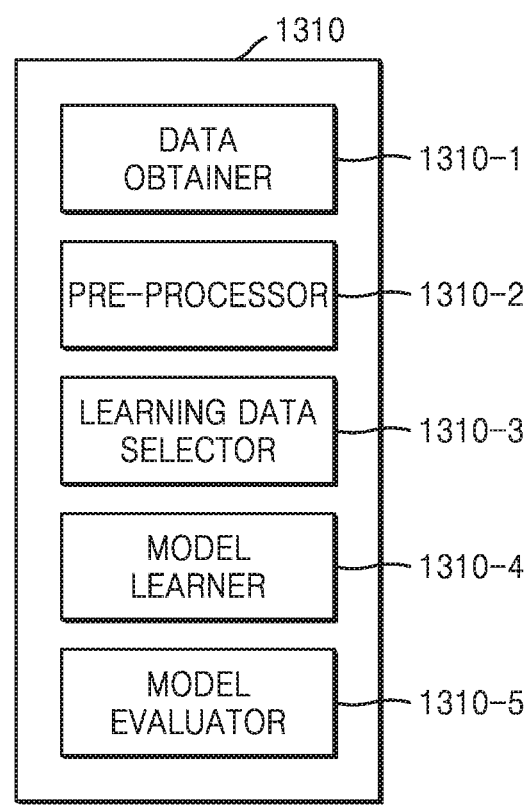
FIG. 28 is a block diagram of a data learner according to an embodiment of the disclosure.

FIG. 28 is a block diagram of the data learner 1310 according to an embodiment of the disclosure.

Referring to FIG. 28, the data learner 1310 according to an embodiment of the disclosure may include a data obtainer 1310-1, a pre-processor 1310-2, a learning data selector 1310-3, a model learner 1310-4, and a model evaluator 1310-5.

The data obtainer 1310-1 may obtain data required for determining a state of an object. The data obtainer 1310-1 may obtain the data (for example, the camera image, the spectrometric image, and the environmental information) required for learning for determining the state of the object. According to an embodiment of the disclosure, the data obtainer 1310-1 may directly generate the data required for determining the state of the object or receive the data required for determining the state of the object from an external device or the server apparatus 2000.

According to an embodiment of the disclosure, the data obtainer 1310-1 may obtain image data, sound data, text data, or biometric signal data. For example, the data obtainer 1310-1 may receive the data through an input device (for example, a microphone, a camera, or a sensor) of the refrigerator 1000. Alternatively, the data obtainer 1310-1 may obtain the data through an external device communicating with the refrigerator 1000.

The pre-processor 1310-2 may pre-process the obtained data so that the obtained data may be used for learning for determining the state of the object. The pre-processor 1310-2 may process the obtained data into a predetermined format so that the model learner 1310-4 to be described below may use the obtained data for learning for determining the state of the object.

For example, the pre-processor 1310-2 may generate one composite image by combining at least a portion of each of a plurality of images, based on a common area included in each of the plurality of images (or frames) forming at least a portion of an input video. In this case, a plurality of composite images may be generated from one video. The common area may be an area including a common object (for example, an object, an animal, a plant, a human being, etc.) which is the same or substantially the same in each of the plurality of images. Alternatively, the common area may be an area in each of the plurality of images, the area having the same or substantially the same color, shadow, RGB value, or CMYK value.

The learning data selector 1310-3 may select the data required for learning from the pre-processed data. The selected data may be provided to the model learner 1310-4. The learning data selector 1310-3 may select the data required for learning from the pre-processed data based on a predetermined reference for determining the state of the object. Also, the learning data selector 1310-3 may select the data based on a reference predetermined by learning of the model learner 1310-4 to be described below.

The model learner 1310-4 may learn a reference as to how to determine the state of the object based on the learning data. Also, the model learner 1310-4 may learn a reference as to which learning data is to be used for determining the state of the object.

Also, the model learner 1310-4 may train the data recognition model used to determine the state of the object by using the learning data. In this case, the data recognition model may be a pre-established model. For example, the data recognition model may be the model pre-established by receiving basic learning data (for example, a sample image, etc.).

The data recognition model may be established by taking into account an application field of the recognition model, the purpose of learning, or the computer performance of a device. The data recognition model may be, for example, a model based on a neural network. For example, models, such as a deep neural network (DNN), a recurrent neural network (RNN), and a bidirectional recurrent deep neural network (BRDNN), may be used as the data recognition model, but it is not limited thereto.

According to various embodiments of the disclosure, when there are a plurality of pre-established data recognition models, the model learner 1310-4 may determine a data recognition model having a great relevance between input learning data and basic learning data as the data recognition model for learning. In this case, the basic learning data may be pre-classified into types of the data and the data recognition model may be pre-established for the types of the data. For example, the basic learning data may be pre-classified based on various references, such as a region in which the learning data is generated, a time in which the learning data is generated, a size of the learning data, a genre of the learning data, a generator of the learning data, a type of an object in the learning data, etc.

Also, the model learner 1310-4 may train the data recognition model by using, for example, learning algorithms, such as error back-propagation and gradient descent.

Also, the model learner 1310-4 may train the data recognition model, for example, through supervised learning in which the learning data is used as an input value. Also, the model learner 1310-4 may train the data recognition model, for example, through unsupervised learning based on which the type of the data required for determining the state of the object is self-trained without a particular instruction to discover a reference for determining the state of the object. Also, the model learner 1310-4 may train the data recognition model, for example, through reinforcement learning based on which feedback about whether a result of determining the state of the object based on learning is correct or not is used.

Also, when the data recognition model is trained, the model learner 1310-4 may store the trained data recognition model. In this case, the model learner 1310-4 may store the trained data recognition model in the memory 1800 of the refrigerator 1000 including the data recognizer 1320. Alternatively, the model learner 1310-4 may store the trained data recognition model in the memory 1800 of the refrigerator 1000 including the data recognizer 1320 to be described below. Alternatively, the model learner 1310-4 may store the trained data recognition model in a memory of the server apparatus 2000 connected with the refrigerator 1000 in a wired or wireless network.

In this case, the memory 1800 in which the trained data recognition model is stored may also store, for example, commands or data related to at least another component of the refrigerator 1000. Also, the memory 1800 may store software and/or programs. The programs may include, for example, kernel, middleware, an application programming interface (API) and/or an application program (or an "application").

The model evaluator 1310-5 may input evaluation data in the data recognition model and, when a recognition result output from the evaluation data does not meet a predetermined reference, the model evaluator 1310-5 may have the model learner 1310-4 re-learn. In this case, the evaluation data may be the data predetermined for evaluating the data recognition model.

For example, the model evaluator 1310-5 may evaluate that the recognition result does not meet the predetermined reference, when the number of pieces of the evaluation data for which the recognition result is not correct or the rate of the evaluation data for which the recognition result is not correct exceeds a predetermined critical value, from among recognition results of the trained data recognition model with respect to the evaluation data. For example, when the predetermined reference is defined as 2% and when the trained data recognition model outputs incorrect recognition results with respect to the pieces of evaluation data that are more than twenty (20) out of the total one thousand (1,000) pieces of evaluation data, the model evaluator 1310-5 may evaluate that the trained data recognition model is not appropriate.

Meanwhile, when there are a plurality of trained data recognition models, the model evaluator 1310-5 may evaluate whether each of the trained data recognition models meets a predetermined reference and may determine the model meeting the predetermined reference as the final data recognition model. In this case, when there are a plurality of models meeting the predetermined reference, the model evaluator 1310-5 may determine one predetermined model or a predetermined number of models as the final data recognition models, based on the order of the score of the evaluation.

Meanwhile, at least one of the data obtainer 1310-1, the pre-processor 1310-2, the learning data selector 1310-3, the model learner 1310-4, or the model evaluator 1310-5 may be formed in the form of at least one hardware chip and may be mounted in the refrigerator 1000. For example, at least one of the data obtainer 1310-1, the pre-processor 1310-2, the learning data selector 1310-3, the model learner 1310-4, or the model evaluator 1310-5 may be formed in the form of an exclusive hardware chip for AI, or may be formed as a part of a general-purpose processor (for example, a CPU or an application processor) or a graphics exclusive processor (for example, a GPU) and may be mounted in the refrigerator 1000.

Also, the data obtainer 1310-1, the pre-processor 1310-2, the learning data selector 1310-3, the model learner 1310-4, and the model evaluator 1310-5 may be mounted in one refrigerator 1000 or each may be mounted in a separate electronic apparatus. For example, some of the data obtainer 1310-1, the pre-processor 1310-2, the learning data selector 1310-3, the model learner 1310-4, and the model evaluator 1310-5 may be included in the refrigerator 1000 and the others may be included in the server apparatus 2000.

Also, at least one of the data obtainer 1310-1, the pre-processor 1310-2, the learning data selector 1310-3, the model learner 1310-4, or the model evaluator 1310-5 may be realized as a software module. When the at least one of the data obtainer 1310-1, the pre-processor 1310-2, the learning data selector 1310-3, the model learner 1310-4, or the model evaluator 1310-5 is realized as the software module (or a program module including an instruction), the software module may be stored in a non-transitory computer readable recording medium. Also, in this case, the at least one software module may be provided by an OS or by a predetermined application. Alternatively, a portion of the at least one software module may be provided by an OS and the other portions of the at least one software module may be provided by a predetermined application.

Figure 29:
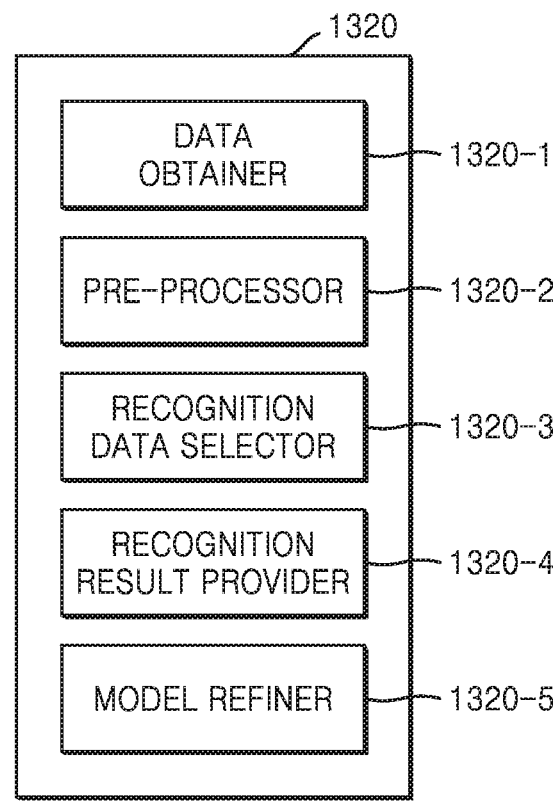
FIG. 29 is a block diagram of a data recognizer according to an embodiment of the disclosure.

FIG. 29 is a block diagram of the data recognizer 1320 according to an embodiment of the disclosure.

Referring to FIG. 29, the data recognizer 1320 according to an embodiment of the disclosure may include a data obtainer 1320-1, a pre-processor 1320-2, a recognition data selector 1320-3, a recognition result provider 1320-4, and a model refiner 1320-5.

The data obtainer 1320-1 may obtain data required for determining a state of an object and the pre-processor 1320-2 may pre-process the obtained data so that the obtained data may be used for determining the state of the object. The pre-processor 1320-2 may process the obtained data into a predetermined format so that the recognition result provider 1320-4 to be described below may use the obtained data to determine the state of the object.

The recognition data selector 1320-3 may select data required for determining the state of the object from the pre-processed data. The selected data may be provided to the recognition result provider 1320-4. The recognition data selector 1320-3 may select part or all of the pre-processed data according to a predetermined reference for determining the state of the object. Also, the recognition data selector 1320-3 may select the data according to a reference predetermined based on learning by the model learner 1310-4 to be described below.

The recognition result provider 1320-4 may determine the state of the object by applying the selected data to the data recognition model. The recognition result provider 1320-4 may provide the recognition result according to the purpose of data recognition. The recognition result provider 1320-4 may apply the selected data to the data recognition model by using the data selected by the recognition data selector 1320-3 as an input value. Also, the recognition result may be determined by the data recognition model.

For example, the recognition result of at least one image may be provided as text, a voice, a video, an image, or an instruction (for example, an application execution instruction, a module function execution instruction, etc.). For example, the recognition result provider 1320-4 may provide a recognition result of an object included in at least one image. The recognition result may include, for example, information about a current state of the object included in the at least one image, information about a change in a state of the object, etc.

The model refiner 1320-5 may allow the data recognition model to be refined based on the evaluation about the recognition result provided by the recognition result provider 1320-4. For example, the model refiner 1320-5 may provide the recognition result provided by the recognition result provider 1320-4 to the model learner 1310-4 to allow the model learner 1310-4 to refine the data recognition model.

Meanwhile, at least one of the data obtainer 1320-1, the pre-processor 1320-2, the recognition data selector 1320-3, the recognition result provider 1320-4, or the model refiner 1320-5 in the data recognizer 1320 may be formed in the form of at least one hardware chip and may be mounted in the refrigerator 1000. For example, at least one of the data obtainer 1320-1, the pre-processor 1320-2, the recognition data selector 1320-3, the recognition result provider 1320-4, or the model refiner 1320-5 may be formed in the form of an exclusive hardware chip for AI or may be formed as a part of a general-purpose processor (for example, a CPU or an application processor) or a graphics exclusive processor (for example, a GPU) and may be mounted in the refrigerator 1000.

Also, the data obtainer 1320-1, the pre-processor 1320-2, the recognition data selector 1320-3, the recognition result provider 1320-4, and the model refiner 1320-5 may be mounted in one refrigerator 1000 or each may be mounted in a separate electronic apparatus. For example, some of the data obtainer 1320-1, the pre-processor 1320-2, the recognition data selector 1320-3, the recognition result provider 1320-4, and the model refiner 1320-5 may be included in the refrigerator 1000 and the others may be included in the server apparatus 2000.

Also, at least one of the data obtainer 1320-1, the pre-processor 1320-2, the recognition data selector 1320-3, the recognition result provider 1320-4, or the model refiner 1320-5 may be realized as a software module. When the at least one of the data obtainer 1320-1, the pre-processor 1320-2, the recognition data selector 1320-3, the recognition result provider 1320-4, or the model refiner 1320-5 is realized as a software module (or a program module including an instruction), the software module may be stored in a non-transitory computer readable recording medium. Also, in this case, the at least one software module may be provided by an OS or by a predetermined application. Alternatively, a portion of the at least one software module may be provided by an OS and the other portions of the at least one software module may be provided by a predetermined application.

Figure 30:
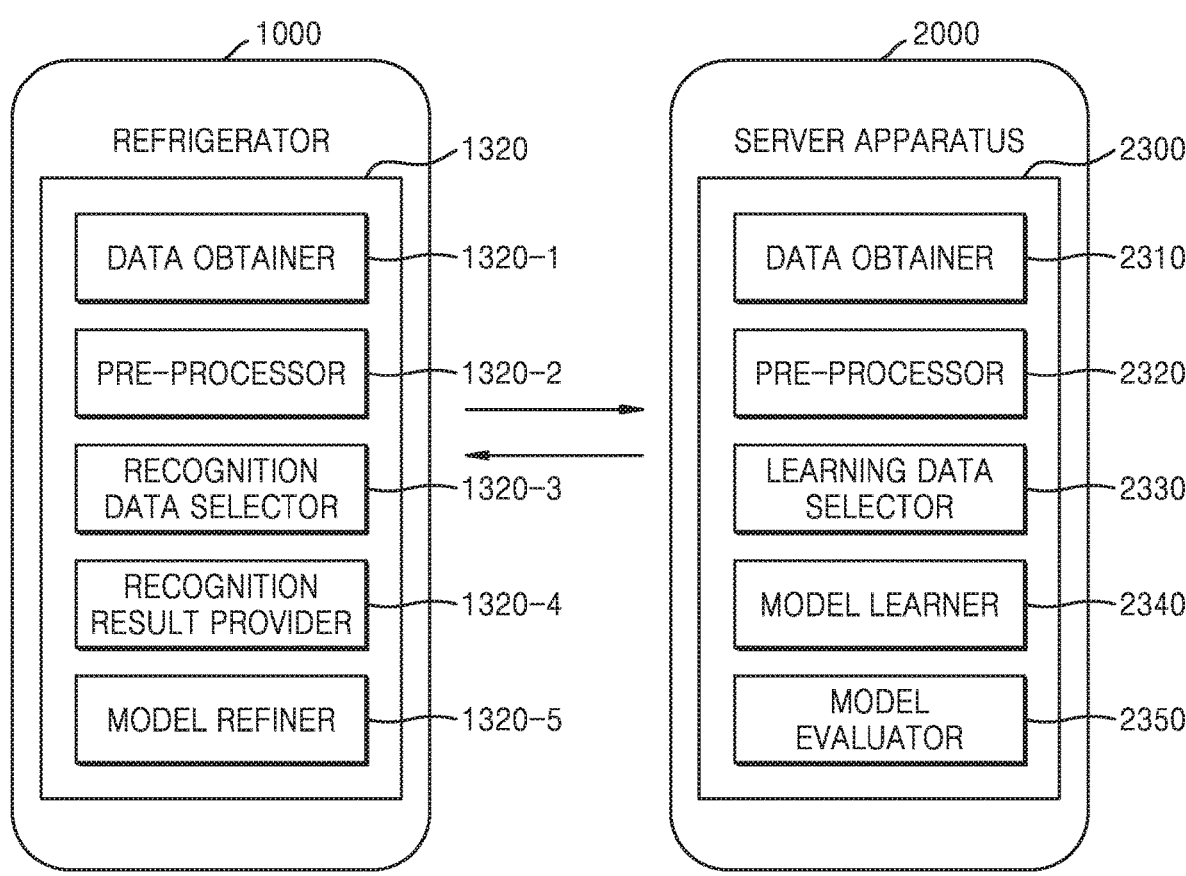
FIG. 30 is a view illustrating an example in which an electronic apparatus and a server learn and recognize data in interconnection with each other, according to an embodiment of the disclosure.

FIG. 30 is a view showing an example in which the refrigerator 1000 and the server apparatus 2000 operate in connection with each other to learn and recognize data, according to an embodiment of the disclosure.

Referring to FIG. 30, the server apparatus 2000 may learn a reference for determining a state of an object and the refrigerator 1000 may determine the state of the object based on a result of learning by the server apparatus 2000.

In this case, a model learner 2340 of the server apparatus 2000 may perform the function of the data learner 1310 illustrated in FIG. 28. The model learner 2340 of the server apparatus 2000 may learn a reference as to which data to use to determine the state of the object and as to how to determine the state of the object by using the data. The model learner 2340 may learn the reference for determining the state of the object by obtaining data to be used for learning and applying the obtained data to a data recognition model to be described below.

Also, the recognition result provider 1320-4 of the refrigerator 1000 may determine the state of the object by applying data selected by the recognition data selector 1320-3 to the data recognition model generated by the server apparatus 2000. For example, the recognition result provider 1320-4 may transmit the data selected by the recognition data selector 1320-3 to the server apparatus 2000 and may request the server apparatus 2000 to apply the data selected by the recognition data selector 1320-3 to the recognition model to determine the state of the object. Also, the recognition result provider 1320-4 may receive information about the state of the object determined by the server apparatus 2000 from the server apparatus 2000.

Alternatively, the recognition result provider 1320-4 of the refrigerator 1000 may receive the recognition model generated by the server apparatus 2000 from the server apparatus 2000 and may determine the state of the object by using the received recognition model. In this case, the recognition result provider 1320-4 of the refrigerator 1000 may apply the data selected by the recognition data selector 1320-3 to the data recognition model received from the server apparatus 2000 to determine the state of the object.

The method according to an embodiment of the disclosure may be implemented in the form of a program command that may be executed through various computer means, and may be recorded in a computer-readable recording medium. The computer-readable recording medium may include program commands, data files, data structures, and the like, alone or in combination. The program commands recorded on the computer-readable recording medium may be those specially designed and configured for the disclosure or may be available to one of ordinary skill in the art of computer software. Examples of the computer-readable recording medium may include magnetic media such as hard disks, floppy disks, and magnetic tapes, optical media such as CD-ROMs and DVDs, magneto-optical media such as floptical disks, and hardware devices specifically configured to store and execute program commands, such as ROM, RAM, flash memory, and the like. Examples of the program command include machine language code such as one produced by a compiler, as well as high-level language code that may be executed by a computer using an interpreter or the like.

The one or more embodiments of the disclosure may be embodied as a recording medium including instructions executable by a computer, such as program modules executed by computers. The computer-readable medium may include any usable medium that may be accessed by computers and may include volatile and non-volatile media, and detachable and non-detachable media. Also, the computer-readable medium may include a computer storage medium and a communication medium. The computer storage medium may include all of volatile and non-volatile media, and detachable and non-detachable media which are realized based on any methods and technologies to store information including computer-readable instructions, data structures, program modules, or other data. The communication medium may typically include computer-readable instructions, data structures, program modules, other data of modified data signals, such as carrier waves, other transmission mechanisms, or other information transmission media. Also, the one or more embodiments of the disclosure may be embodied as a computer program or a computer program product including instructions executable by a computer.

While the embodiments of the disclosure have been described in detail, it will be understood by one of ordinary skill in the art that various changes in form and details may be made therein without departing from the spirit and scope of the disclosure as defined by the following claims.

What is claimed is:

1. A method of providing information related to a state of an object in a refrigerator, the method comprising:
    obtaining at least one camera image by using a camera arranged in the refrigerator at a predetermined image detection interval;
    identifying a first camera image at a first time point from the at least one camera image, wherein the first camera image comprises at least one object kept in the refrigerator;
    obtaining environmental information in the refrigerator through an environmental sensor arranged in the refrigerator;
    determining information related to a current state of the at least one object and predicting information related to a future state of the at least one object by applying the first camera image comprising the at least one object, a camera image comprising the at least one object and obtained through the camera at a past time point earlier than the first time point and the environmental information in the refrigerator to an artificial intelligence (AI) model, the first camera image being obtained at the predetermined image detection interval of the camera from the past time point; and
    providing the information related to the current state of the at least one object and the information related to the future state of the at least one object,
    wherein the method further comprises adjusting the predetermined image detection interval of the camera for a second camera image to be obtained through the camera at a second time point later than the first time point based on the information related to the current state of the at least one object, a state change of the at least one object between the past time point and the first time point or the predicted information related to the future state of the at least one object.

2. The method of claim 1, wherein the providing of the information related to the current state of the at least one object and the information related to the future state of the at least one object comprises:
    providing information about a consumable period of the at least one object.

3. The method of claim 1, wherein the providing of the information related to the current state of the at least one object and the information related to the future state of the at least one object comprises:
    providing information about a ripeness or a freshness of the at least one object.

4. The method of claim 1, wherein the environmental sensor comprises at least one of a temperature sensor, a humidity sensor, or an odor sensor, and
    the obtaining of the environmental information in the refrigerator comprises obtaining at least one of temperature information, humidity information, or odor information in the refrigerator.

5. The method of claim 1, wherein the obtaining of the environmental information in the refrigerator comprises obtaining temperature information of a temperature around the at least one object by using a temperature sensor, and
    the determining of the information related to the current state of the at least one object and the predicting of the information related to the future state of the at least one object comprise determining the information related to the current state of the at least one object and predicting the information related to the future state of the at least one object by applying the first camera image, the camera image obtained at the past time point and the temperature information to the AI model.

6. The method of claim 1, wherein the obtaining of the environmental information in the refrigerator comprises obtaining odor information of the at least one object by using an odor sensor arranged to be adjacent to the at least one object, and
    the determining of the information related to the current state of the at least one object and the predicting of the information related to the future state of the at least one object comprise determining the information related to the current state of the at least one object and predicting the information related to the future state of the at least one object by applying the first camera image, the camera image obtained at the past time point and the odor information to the AI model.

7. A method of providing information related to a state of an object in a refrigerator, the method comprising:
    obtaining at least one camera image by using a camera arranged in the refrigerator at a predetermined image detection interval;
    identifying a first camera image at a first time point among the at least one camera image, the identified first camera image comprising at least one object kept in the refrigerator;
    obtaining environmental information in the refrigerator through an environmental sensor arranged in the refrigerator;
    based on a value of the obtained environmental information being greater than a critical value, obtaining a spectrometric image with respect to the at least one object by using a spectrometric sensor arranged in the refrigerator, and based on the value of the obtained environmental information not being greater than the critical value, keeping the obtaining of the environmental information through the environmental sensor;
    determining information related to a current state of the at least one object and predicting information related to a future state of the at least one object by applying the first camera image, the spectrometric image, and the environmental information in the refrigerator to an AI model; and
    providing the information related to the current state of the at least one object and the information related to the future state of the at least one object,
    wherein the method further comprises adjusting the predetermined image detection interval of the camera for a second camera image to be obtained through the camera at a second time point later than the first time point based on the information related to the current state of the at least one object, a state change of the at least one object between a past time point earlier than the first time point and the first time point or the predicted information related to the future state of the at least one object.

8. The method of claim 1, wherein the determining of the information related to the current state of the at least one object and the predicting of the information related to the future state of the at least one object comprise:
   determining whether a gas detection quantity measured by at least one odor sensor from among a plurality of odor sensors arranged in the refrigerator exceeds a critical value;
   when the gas detection quantity exceeds the critical value, generating an odor distribution map based on odor information obtained from the plurality of odor sensors; and
   comparing the first camera image comprising the at least one object with the odor distribution map and identifying a first object of the at least one object including a spoilage probability that is greater than a reference value.

9. The method of claim 8, wherein the identifying of the first object comprises:
   obtaining spectrometric information about the first object by using a spectrometric sensor arranged in the refrigerator; and
   determining a degree of spoilage of the first object by using the spectrometric information.

10. The method of claim 8, further comprising:
    when the first object is totally or partially hidden by a second object of the at least one object in the first camera image, providing notification information about a location where the first object is kept in the refrigerator.

11. The method of claim 8, further comprising:
    controlling a position of the camera to capture the identified first object.

12. The method of claim 1, wherein the adjusting of the predetermined image detection interval of the camera includes obtaining a value indicating a predicted state change of the at least one object at the second time point and adjusting the predetermined image detection interval of the camera based on the value indicating the predicted state change of the at least one object.

13. A refrigerator comprising:
    a camera configured to obtain at least one camera image comprising at least one object kept in the refrigerator;
    an environmental sensor configured to obtain environmental information in the refrigerator;
    a processor configured to identify a first camera image obtained at a first time point, determine information related to a current state of the at least one object and to predict information related to a future state of the at least one object by applying the first camera image, a camera image comprising the at least one object and obtained though the camera at a past time point earlier than the first time point and the environmental information in the refrigerator to an artificial intelligence (AI) model, the first camera image being obtained at a predetermined image detection interval of the camera from the past time point; and
    an outputter configured to provide the information related to the current state of the at least one object and the information related to the future state of the at least one object,
    wherein the processor is configured to adjust the predetermined image detection interval of the camera for a second camera image to be obtained through the camera at a second time point later than the first time point based on the information related to the current state of the at least one object, a state change of the at least one object between the past time point and the first time point or the predicted information related to the future state of the at least one object.

14. The refrigerator of claim 13, wherein the information related to the current state of the at least one object and the information related to the future state of the at least one object comprise at least one of information about a consumable period of the at least one object, information about a ripeness of the at least one object, or information about a freshness of the at least one object.

15. The refrigerator of claim 13, wherein the environmental sensor comprises a temperature sensor, and
    the processor is further configured to:
    obtain temperature information of a temperature around the at least one object by using the temperature sensor, and
    determine the information related to the current state of the at least one object and predict the information related to the future state of the at least one object by applying the first camera image, the camera image obtained at the past time point and the temperature information to the AI model.

16. The refrigerator of claim 13, wherein the environmental sensor comprises an odor sensor arranged to be adjacent to the at least one object, and
    the processor is further configured to:
    obtain odor information of the at least one object by using the odor sensor, and
    determine the information related to the current state of the at least one object and predict the information related to the future state of the at least one object by applying the first camera image comprising the at least one object, the camera image obtained at the past time point and the odor information of the at least one object to the AI model.

17. A refrigerator comprising:
    a camera arranged in the refrigerator;
    a spectrometric sensor configured to obtain a spectrometric image about at least one object in the refrigerator;
    an environmental sensor configured to obtain environmental information in the refrigerator; and
    a processor configured to control the camera to obtain at least one camera image at a predetermined image detection interval, identify a first camera image at a first time point among the at least one camera image, the identified first camera image comprising the at least one object, determine information related to a current state of the at least one object and predict information related to a future state of the at least one object by applying the first camera image, the spectrometric image, and the environmental information in the refrigerator to an AI model and provide the information related to the current state of the at least one object and the information related to the future state of the at least one object,
    wherein the processor is further configured to control the spectrometric sensor to obtain the spectrometric image about the at least one object based on a value of the obtained environmental information being greater than a critical value, and control the environmental sensor to keep obtaining the environmental information in the refrigerator based on the value of the obtained environmental information not being greater than the critical value, and wherein the processor is further configured to adjust the predetermined image detection interval of the camera for a second camera image to be obtained through the camera at a second time point later than the first time point based on the information related to the current state of the at least one object, a state change of the at least one object between a past time point earlier than the first time point and the first time point or the predicted information related to the future state of the at least one object.

18. The refrigerator of claim 13, wherein the processor is further configured to:
  determine whether a gas detection quantity measured by at least one odor sensor from among a plurality of odor sensors arranged in the refrigerator exceeds a critical value,
  generate an odor distribution map based on odor information obtained from the plurality of odor sensors, when the gas detection quantity exceeds the critical value, and
  compare the first camera image comprising the at least one object with the odor distribution map and identify a first object of the at least one object including a spoilage probability that is greater than a reference value.

19. The refrigerator of claim 18, wherein the processor is further configured to:
  obtain spectrometric information about the first object by using a spectrometric sensor arranged in the refrigerator, and
  determine a degree of spoilage of the first object by using the spectrometric information.

20. A computer program product comprising a non-transitory computer readable medium having recorded thereon a program to execute a method comprising:
  an operation of obtaining at least one camera image by using a camera arranged in a refrigerator at a predetermined image detection interval;
  an operation of identifying a first camera image at a first time point from the at least one camera image, wherein the first camera image comprises at least one object kept in the refrigerator,
  an operation of obtaining environmental information in the refrigerator through an environmental sensor arranged in the refrigerator,
  an operation of determining information related to a current state of the at least one object and predicting information related to a future state of the at least one object by applying the first camera image comprising the at least one object, a camera image comprising the at least one object and obtained through the camera at a past time point earlier than the first time point and the environmental information in the refrigerator to an artificial intelligence (AI) model, the first camera image being obtained at the predetermined image detection interval of the camera from the past time point, and
  an operation of providing the information related to the current state of the at least one object and the information related to the future state of the at least one object,
  wherein the method further comprises an operation of adjusting the predetermined image detection interval of the camera for a second camera image be obtained through the camera at a second time point later than the first time point based on the information related to the current state of the at least one object, a state change of the at least one object between the past time point and the first time point or the predicted information related to the future state of the at least one object.

21. The refrigerator of claim 13, wherein the processor is configured to obtain a value indicating a predicted state change of the at least one object at the second time point and adjust the predetermined image detection interval of the camera based on the value indicating the predicted state change of the at least one object.

22. The computer program product of claim 20, wherein the operation of adjusting the predetermined image detection interval of the camera includes obtaining a value indicating a predicted state change of the at least one object at the second time point and adjusting the predetermined image detection interval of the camera based on the value indicating the predicted state change of the at least one object.

* * * * *